(12) United States Patent
Truckai et al.

(10) Patent No.: US 7,955,331 B2
(45) Date of Patent: Jun. 7, 2011

(54) ELECTROSURGICAL INSTRUMENT AND METHOD OF USE

(75) Inventors: Csaba Truckai, Saratoga, CA (US); John H. Shadduck, Tiburon, CA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 933 days.

(21) Appl. No.: 11/080,101

(22) Filed: Mar. 14, 2005

(65) Prior Publication Data
US 2005/0203507 A1    Sep. 15, 2005

Related U.S. Application Data

(60) Provisional application No. 60/552,978, filed on Mar. 12, 2004.

(51) Int. Cl.
*A61B 18/14* (2006.01)
(52) U.S. Cl. .............................. 606/51; 606/50; 606/52
(58) Field of Classification Search .............. 606/27–31, 606/41, 48–50
See application file for complete search history.

(56) References Cited

U.S. PATENT DOCUMENTS

| | | | |
|---|---|---|---|
| 659,409 A | 10/1900 | Mosher | |
| 1,586,645 A | 6/1926 | Bierman | |
| 1,798,902 A | 3/1931 | Raney | |
| 1,881,250 A | 10/1932 | Tomlinson | |
| 2,031,682 A | 2/1936 | Wappler et al. | |
| 3,243,753 A | 3/1966 | Kohler | |
| 3,651,811 A | 3/1972 | Hildebrandt et al. | |
| 3,685,518 A | 8/1972 | Beuerle et al. | |
| 3,730,188 A | 5/1973 | Ellman | |
| 3,752,161 A | 8/1973 | Bent | |
| 3,762,482 A | 10/1973 | Johnson | |
| 3,768,482 A | 10/1973 | Shaw | |
| 3,826,263 A | 7/1974 | Cage et al. | |
| 4,092,986 A | 6/1978 | Schneiderman | |
| 4,198,957 A | 4/1980 | Cage et al. | |
| 4,219,025 A | 8/1980 | Johnson | |

(Continued)

FOREIGN PATENT DOCUMENTS

EP        341446        11/1989

(Continued)

OTHER PUBLICATIONS

Corson, S.L., "Two new laparoscopic instruments: Biopolar sterilizing forceps and uterine manipulator", Medical Instrumentation, 11(1):7-8 (1977).

(Continued)

*Primary Examiner* — Michael Peffley
*Assistant Examiner* — Ronald Hupczey, Jr.
(74) *Attorney, Agent, or Firm* — Verne E. Kreger, Jr.

(57) ABSTRACT

A particular embodiment of the invention provides an electrosurgical working end for performing high strength welding of tissue comprising a body having a tissue contacting energy delivery surface. The body includes pixel portions and non-pixel portions distributed within the tissue contacting surface. The pixel portions comprise a positive temperature coefficient of resistance (PTCR) material with at least one pixel portion configured to switch Rf current on and off in the at least one pixel portion responsive to tissue temperature adjacent the at least one pixel portion. The pixel portions can be configured to be coupled to an Rf current source such as an Rf generator. The pixelated energy delivery surfaces are capable of highly localized modulation of Rf energy application to the engaged tissue to create high strength tissue welds.

22 Claims, 31 Drawing Sheets

U.S. PATENT DOCUMENTS

| | | |
|---|---|---|
| 4,231,371 A | 11/1980 | Lipp |
| 4,232,676 A | 11/1980 | Herczog |
| 4,237,441 A | 12/1980 | van Konynenburg et al. |
| 4,271,838 A | 6/1981 | Lasner et al. |
| 4,304,987 A | 12/1981 | van Konynenburg |
| 4,353,371 A | 10/1982 | Cosman |
| 4,370,980 A | 2/1983 | Lottick |
| 4,375,218 A | 3/1983 | DiGeronimo |
| 4,492,231 A | 1/1985 | Auth |
| 4,545,926 A | 10/1985 | Fouts, Jr. et al. |
| 4,590,934 A | 5/1986 | Malis et al. |
| 4,608,981 A | 9/1986 | Rothfuss et al. |
| 4,633,874 A | 1/1987 | Chow et al. |
| 4,654,511 A | 3/1987 | Horsma et al. |
| 4,655,216 A | 4/1987 | Tischer |
| 4,671,274 A | 6/1987 | Sorochenko |
| 4,691,703 A | 9/1987 | Auth et al. |
| 4,763,669 A | 8/1988 | Jaeger |
| 4,785,807 A | 11/1988 | Blanch |
| 4,799,479 A | 1/1989 | Spears |
| 4,848,337 A | 7/1989 | Shaw et al. |
| 4,849,133 A | 7/1989 | Yoshida et al. |
| 4,850,353 A | 7/1989 | Stasz et al. |
| 4,887,612 A | 12/1989 | Esser et al. |
| 4,910,389 A | 3/1990 | Sherman et al. |
| 4,930,494 A | 6/1990 | Takehana et al. |
| 4,940,468 A | 7/1990 | Petillo |
| 4,958,539 A | 9/1990 | Stasz et al. |
| 4,969,885 A | 11/1990 | Farin |
| 4,971,068 A | 11/1990 | Sahi |
| 4,985,030 A | 1/1991 | Melzer et al. |
| 5,009,656 A | 4/1991 | Reimels |
| 5,057,106 A | 10/1991 | Kasevich et al. |
| 5,057,107 A | 10/1991 | Parins et al. |
| 5,085,659 A | 2/1992 | Rydell |
| 5,086,586 A | 2/1992 | Hlavaty et al. |
| 5,104,025 A | 4/1992 | Main et al. |
| 5,106,538 A | 4/1992 | Barma et al. |
| 5,122,137 A | 6/1992 | Lennox |
| 5,147,356 A | 9/1992 | Bhatta |
| 5,147,357 A | 9/1992 | Rose et al. |
| 5,151,102 A | 9/1992 | Kamiyama et al. |
| 5,201,900 A | 4/1993 | Nardella |
| 5,207,691 A | 5/1993 | Nardella |
| 5,217,460 A | 6/1993 | Knoepfler |
| 5,258,006 A | 11/1993 | Rydell et al. |
| 5,267,998 A | 12/1993 | Hagen |
| 5,269,780 A | 12/1993 | Roos |
| 5,290,286 A | 3/1994 | Parins |
| 5,306,280 A | 4/1994 | Bregen et al. |
| 5,308,311 A | 5/1994 | Eggers et al. |
| 5,318,565 A | 6/1994 | Kuriloff et al. |
| 5,324,289 A | 6/1994 | Eggers |
| 5,336,221 A | 8/1994 | Anderson |
| 5,360,428 A | 11/1994 | Hutchinson, Jr. |
| 5,364,389 A | 11/1994 | Anderson |
| 5,382,384 A | 1/1995 | Baigrie et al. |
| 5,389,098 A | 2/1995 | Tsuruta et al. |
| 5,395,369 A | 3/1995 | McBrayer et al. |
| 5,403,312 A | 4/1995 | Yates et al. |
| 5,417,687 A | 5/1995 | Nardella et al. |
| 5,445,638 A | 8/1995 | Rydell et al. |
| 5,451,224 A | 9/1995 | Goble et al. |
| 5,458,598 A | 10/1995 | Feinberg et al. |
| 5,480,397 A | 1/1996 | Eggers et al. |
| 5,480,398 A | 1/1996 | Eggers |
| 5,507,106 A | 4/1996 | Fox |
| 5,529,235 A | 6/1996 | Boiarski et al. |
| 5,531,744 A | 7/1996 | Nardella et al. |
| 5,571,153 A | 11/1996 | Wallsten |
| 5,573,535 A | 11/1996 | Viklund |
| 5,582,611 A | 12/1996 | Tsuruta et al. |
| 5,593,406 A | 1/1997 | Eggers et al. |
| 5,595,689 A | 1/1997 | Kulkarni et al. |
| 5,603,825 A | 2/1997 | Costinel |
| 5,611,798 A | 3/1997 | Eggers |
| 5,624,452 A | 4/1997 | Yates |
| 5,665,100 A | 9/1997 | Yoon |
| 5,674,220 A | 10/1997 | Fox et al. |
| 5,693,051 A | 12/1997 | Schulze et al. |
| 5,716,366 A | 2/1998 | Yates |
| 5,735,848 A | 4/1998 | Yates et al. |
| 5,755,717 A | 5/1998 | Yates et al. |
| 5,766,166 A | 6/1998 | Hooven |
| 5,776,130 A | 7/1998 | Buysse et al. |
| 5,797,938 A | 8/1998 | Paraschac et al. |
| 5,800,449 A | 9/1998 | Wales |
| 5,807,392 A | 9/1998 | Eggers |
| 5,833,690 A | 11/1998 | Yates et al. |
| 5,836,874 A | 11/1998 | Swanson et al. |
| 5,849,011 A | 12/1998 | Jones et al. |
| 5,880,668 A | 3/1999 | Hall |
| 5,891,142 A | 4/1999 | Eggers et al. |
| 5,897,142 A | 4/1999 | Kulevsky |
| 5,911,719 A | 6/1999 | Eggers |
| 5,947,984 A | 9/1999 | Whipple |
| 5,980,485 A | 11/1999 | Grantz et al. |
| 6,019,758 A | 2/2000 | Slater |
| 6,030,384 A | 2/2000 | Nezhat |
| 6,032,674 A * | 3/2000 | Eggers et al. .................. 128/898 |
| 6,039,733 A | 3/2000 | Buysse et al. |
| 6,059,778 A * | 5/2000 | Sherman ........................ 606/34 |
| 6,074,389 A | 6/2000 | Levine et al. |
| 6,086,586 A | 7/2000 | Hooven |
| 6,106,558 A | 8/2000 | Picha |
| 6,107,699 A | 8/2000 | Swanson |
| 6,113,598 A | 9/2000 | Baker |
| H1904 H | 10/2000 | Yates et al. |
| 6,132,426 A | 10/2000 | Kroll |
| 6,139,508 A | 10/2000 | Simpson |
| 6,143,207 A | 11/2000 | Yamada et al. |
| 6,152,923 A | 11/2000 | Ryan |
| 6,162,220 A | 12/2000 | Nezhat |
| 6,174,309 B1 | 1/2001 | Wrublewski et al. |
| 6,176,857 B1 | 1/2001 | Ashley |
| 6,179,834 B1 | 1/2001 | Buysse et al. |
| 6,179,835 B1 | 1/2001 | Panescu et al. |
| 6,179,837 B1 | 1/2001 | Hooven |
| 6,187,003 B1 | 2/2001 | Buysse et al. |
| 6,190,386 B1 | 2/2001 | Rydell |
| 6,193,709 B1 | 2/2001 | Miyawaki et al. |
| 6,270,497 B1 | 8/2001 | Sekino et al. |
| 6,273,887 B1 | 8/2001 | Yamauchi et al. |
| 6,277,117 B1 | 8/2001 | Tetzlaff et al. |
| 6,277,177 B1 | 8/2001 | Bley et al. |
| 6,296,640 B1 | 10/2001 | Wampler et al. |
| 6,298,550 B1 | 10/2001 | Kirwan, Jr. |
| 6,328,703 B1 | 12/2001 | Murakami |
| 6,334,861 B1 | 1/2002 | Chandler et al. |
| 6,350,264 B1 | 2/2002 | Hooven |
| 6,352,536 B1 | 5/2002 | Buysse et al. |
| 6,398,779 B1 | 6/2002 | Buysse et al. |
| 6,409,725 B1 | 6/2002 | Khandkar et al. |
| 6,451,018 B1 | 9/2002 | Lands et al. |
| 6,457,018 B1 | 9/2002 | Rubin |
| 6,458,127 B1 | 10/2002 | Truckai et al. |
| 6,458,128 B1 | 10/2002 | Schulze |
| 6,458,130 B1 | 10/2002 | Frazier et al. |
| 6,464,702 B2 | 10/2002 | Schulze et al. |
| 6,464,704 B2 | 10/2002 | Schmaltz et al. |
| 6,468,275 B1 | 10/2002 | Wampler et al. |
| 6,485,436 B1 | 11/2002 | Truckai et al. |
| 6,492,629 B1 | 12/2002 | Sopory |
| 6,500,176 B1 | 12/2002 | Truckai et al. |
| 6,511,480 B1 | 1/2003 | Tetzlaff et al. |
| 6,527,767 B2 | 3/2003 | Wang et al. |
| 6,533,784 B2 | 3/2003 | Truckai et al. |
| 6,554,829 B2 | 4/2003 | Schulze et al. |
| 6,575,968 B1 | 6/2003 | Eggers et al. |
| 6,585,735 B1 | 7/2003 | Frazier et al. |
| 6,602,252 B2 | 8/2003 | Mollenauer |
| 6,632,193 B1 | 10/2003 | Davison et al. |
| 6,652,521 B2 | 11/2003 | Schulze |
| 6,656,177 B2 | 12/2003 | Truckai et al. |
| 6,770,072 B1 | 8/2004 | Truckai et al. |
| 6,773,409 B2 | 8/2004 | Truckai et al. |
| 6,802,843 B2 | 10/2004 | Truckai et al. |

| | | |
|---|---|---|
| 6,808,525 B2 | 10/2004 | Latterell et al. |
| 6,835,199 B2 | 12/2004 | McGuckin, Jr. et al. |
| 6,843,789 B2 | 1/2005 | Goble |
| 6,890,332 B2 | 5/2005 | Truckai et al. |
| 6,893,435 B2 | 5/2005 | Goble |
| 6,905,497 B2 | 6/2005 | Truckai et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 7,011,657 B2 | 3/2006 | Truckai et al. |
| 7,041,102 B2 | 5/2006 | Truckai et al. |
| 7,070,597 B2 | 7/2006 | Truckai et al. |
| 7,083,619 B2 | 8/2006 | Truckai et al. |
| 7,087,054 B2 | 8/2006 | Truckai et al. |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,169,147 B2 | 1/2007 | Nosel |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Asafusa et al. |
| 7,381,209 B2 | 6/2008 | Truckai et al. |
| 7,632,269 B2 | 12/2009 | Truckai et al. |
| 2002/0052599 A1 | 5/2002 | Goble |
| 2002/0107517 A1 | 8/2002 | Witt et al. |
| 2002/0115997 A1 | 8/2002 | Truckai et al. |
| 2002/0120261 A1* | 8/2002 | Morris et al. ............ 606/41 |
| 2002/0120266 A1 | 8/2002 | Truckai et al. |
| 2002/0169392 A1 | 11/2002 | Truckai et al. |
| 2002/0177848 A1 | 11/2002 | Truckai et al. |
| 2003/0018327 A1 | 1/2003 | Truckai et al. |
| 2003/0027028 A1 | 2/2003 | Davis |
| 2003/0050635 A1 | 3/2003 | Truckai et al. |
| 2003/0055417 A1 | 3/2003 | Truckai et al. |
| 2003/0069579 A1 | 4/2003 | Truckai et al. |
| 2003/0078573 A1* | 4/2003 | Truckai et al. ............ 606/41 |
| 2003/0078577 A1* | 4/2003 | Truckai et al. ............ 606/51 |
| 2003/0078578 A1 | 4/2003 | Truckai et al. |
| 2003/0088243 A1* | 5/2003 | Carmel et al. ............ 606/41 |
| 2003/0114851 A1 | 6/2003 | Truckai et al. |
| 2003/0125727 A1 | 7/2003 | Truckai et al. |
| 2003/0139741 A1* | 7/2003 | Goble et al. ............ 606/48 |
| 2003/0144652 A1 | 7/2003 | Baker et al. |
| 2003/0171748 A1* | 9/2003 | Truckai et al. ............ 606/51 |
| 2003/0199870 A1 | 10/2003 | Truckai et al. |
| 2003/0208201 A1* | 11/2003 | Iida et al. ............ 606/51 |
| 2003/0212444 A1 | 11/2003 | Truckai et al. |
| 2003/0216733 A1 | 11/2003 | McClurken et al. |
| 2003/0220637 A1 | 11/2003 | Truckai et al. |
| 2005/0096651 A1 | 5/2005 | Truckai et al. |
| 2005/0203507 A1 | 9/2005 | Truckai et al. |
| 2006/0000823 A1 | 1/2006 | Truckai et al. |
| 2006/0293656 A1 | 12/2006 | Shadduck et al. |
| 2007/0106295 A1 | 5/2007 | Garrison et al. |
| 2007/0146113 A1 | 6/2007 | Truckai et al. |
| 2009/0076506 A1 | 3/2009 | Baker |

FOREIGN PATENT DOCUMENTS

| | | |
|---|---|---|
| EP | 517244 | 12/1992 |
| EP | 518230 | 12/1992 |
| EP | 730282 | 9/1996 |
| EP | 1769765 | 4/2007 |
| EP | 1769767 | 4/2007 |
| FR | 2536924 | 6/1984 |
| FR | 2647683 | 12/1990 |
| GB | 2037167 | 7/1980 |
| GB | 2066104 | 7/1981 |
| GB | 2161082 | 1/1984 |
| GB | 2133290 | 7/1984 |
| JP | 05-337129 | 12/1993 |
| JP | 10-033551 | 2/1998 |
| JP | 10-118092 | 5/1998 |
| JP | 2001057302 | 2/2001 |
| JP | 2001-170069 | 6/2001 |
| SU | 342617 | 6/1972 |
| SU | 575103 | 5/1977 |
| WO | 93/08754 | 5/1993 |
| WO | 94/24949 | 11/1994 |
| WO | 94/24951 | 11/1994 |
| WO | 00/09190 | 2/2000 |

OTHER PUBLICATIONS

Burton, J.D.K., "New Inventions", The Lancet, pp. 650-651 (1959).

Nardella, P.C., "Radio Frequency Energy and Impedance Feedback", Proc. SPIE, Catheter-Based Sensing and Imaging Technology, 1068: 42-48 (1989).

Vallfors et al., "Automatically controlled bipolar electrocoagulation—COA-COMP", Neurosurg Rev., 187-190 (1984).

Mayeaux, Jr., "Loop Electrosurgical Excisional Procedure (LEEP) History and Principles", AAFP Colposcopy Course—1994, Louisianna State University Medical Center Shreveport, Louisiana, downloaded from the Internet, http://libsh.lsuhsc.edu/fammed/grounds/leephx.html, 3 pages total.

Smith et al., "Electrosurgery in Otolaryngology—Head and Neck Surgery: Pinciples, Advances, and Complications", Laryngoscope May 2001; 111(5):769-80.

Valleylab, "Biopolar Electrosurgery", retrieved from the Internet, http://www.valleylab.com/education/poes/poes 05.html, copyright 2005, 1 page.

Valleylab, "Electrosurgical Tissue Effect—Electrosurgical Cutting", retrieved from the Internet, http://www.valleylab.com/education/poes/poes_08.html, copyright 2005, 2 pages.

Valleylab, "Principles of Electrosurgery—Electrocautery", retrieved from the Internet, http://www.valleylab.com/education/poes/poes 02.html, copyright2005, 2 pages.

International Search Report from corresponding application PCT/US04/39251 dated Jan. 18, 2006.

International Search Report from related application PCT/US09/052797 dated Oct. 29, 2009.

Office Action in corresponding Japanese patent application JP2003-561406 mailed Feb. 23, 2010.

International Search Report from corresponding application PCT/US08/076683 dated Nov. 25, 2008.

\* cited by examiner

ELECTROSURGICAL INSTRUMENT AND METHOD OF USE

CROSS-REFERENCES TO RELATED APPLICATIONS

This applications claims the benefit of priority of U.S. Provisional Application No. 60/552,978, filed on Mar. 12, 2004, the full disclosure of which is incorporated herein by reference. This application is also related to U.S. patent application Ser. No. 10/032,867 filed Oct. 22, 2001 now U.S. Pat. No. 6,929,644, titled Electrosurgical Jaws Structure for Controlled Energy Delivery, U.S. patent application Ser. No. 10/351,449 filed Jan. 22, 2003 now U.S. Pat. No. 7,112,201, titled Electrosurgical Instrument and Method of Use, U.S. patent application Ser. No. 10/443,974, filed May 22, 2003 now U.S. Pat. No. 7,041,102, titled Electrosurgical Working End with Replaceable Cartridges, and Provisional U.S. Patent Application Ser. No. 60/523,567, filed Nov. 19, 2003 titled Electrosurgical Instrument and Method of Use, all of which are fully incorporated herein by reference.

BACKGROUND OF THE INVENTION

Field of the Invention

Embodiments of the invention relate to an electrosurgical jaw structure. More particularly, embodiments related to a jaw structure with a pixelated energy delivery surface wherein the pixels comprise a positive temperature coefficient of resistance (PTCR) polymeric composition.

Various energy sources such as radiofrequency (Rf) sources, ultrasound sources and lasers have been developed to coagulate, seal or join together tissues volumes in open and laparoscopic surgeries. One area of surgical application relate for such energy sources includes sealing blood vessels which contain considerable fluid pressure therein. Generally, surgical instrument working ends using these energy source have not proven reliable in creating "tissue welds" or "tissue fusion" that provide very high strength immediately welds or seals post-treatment. For this reason, the commercially available instruments, typically powered by Rf or ultrasound, are mostly limited to use in sealing small blood vessels and tissues masses with microvasculature therein.

Further, the commercial Rf surgical devices fail to produce seals with substantial strength in anatomic structures having walls with irregular or thick fibrous content, in bundles of disparate anatomic structures, in substantially thick anatomic structures, and in tissues with thick fascia layers (e.g., large diameter blood vessels).

The effect of RF waves was first reported by d'Arsonval in 1891. (see d'Arsonval, M. A., Action physiologique des courants alternatifs; *CR Soc Biol.;* 1891; 43:283-286). He described heating of tissue when the Rf waves pass through living tissue. This led to the development of medical diathermy. The physical principles of tissue interaction with Rf waves was analyzed in more detail by Organ, who demonstrated that alternating current causes agitation of ions in the living tissue that results in frictional heat and thermal effects (see Organ, L. W., Electrophysiologic principles of radiofrequency lesion making. *Appl Neurophysiol.;* 1976; 39:69-76). A typical Rf system consists of a very high frequency (200 to 1200 KHz) alternating current generator, an Rf monopolar electrode and ground pad (a large dispersive electrode) or a bi-polar electrode arrangement, with the electrodes and targeted tissue all connected in series. In such a circuit, Rf current enters through both the electrodes with the engaged tissue functioning as a resistor component. As the Rf current alternates in directions at high frequency, tissue ions that are attempting to follow the direction of the current are agitated. Due to natural high resistivity in the living tissue, ionic agitation produces frictional heat in tissue captured between bi-polar electrodes in a working end. In a monopolar electrode, because the grounding pad has a very large surface area, the electrical resistance is low at the ground pad and hence the ionic frictional heat is concentrated about the mono-polar electrode's contact with tissue.

Thus, the application of electromagnetic energy from Rf current produces thermal effects, the extent of which are dependent on temperature and Rf application duration. At a targeted temperature range between about 70° C. and 90° C., there occurs heat-induced denaturation of proteins. At any temperature above about 100° C., the tissue will vaporize and tissue carbonization can result.

In a basic jaw structure with a bi-polar electrode arrangement, each face of opposing first and second jaws comprises an electrode and Rf current flows across the captured tissue between the opposing polarity electrodes. Such prior art Rf jaws that engage opposing sides of tissue typically cannot cause uniform thermal effects in the tissue—whether the captured tissue is thin or substantially thick. As Rf energy density in tissue increases, the tissue surface becomes desiccated and resistant to additional ohmic heating. Localized tissue desiccation and charring can occur almost instantly as tissue impedance rises, which then can result in a non-uniform seal in the tissue. The typical prior art Rf jaws can cause further undesirable effects by propagating Rf density laterally from the engaged tissue thus causing unwanted collateral thermal damage.

Commercially available Rf sealing instruments typically attempt to use "power adjustment" approach to control Rf flux in tissue wherein a system controller rapidly adjusts the level of total power delivered to the jaws' electrodes in response to feedback circuitry coupled to the electrodes that measures tissue impedance or electrode temperature. Another approach consists of jaws designs that provide spaced apart or offset electrodes wherein the opposing polarity electrode portions are spaced apart by an insulator material—which may cause current to flow within an extended path through captured tissue rather that simply between opposing electrode surfaces of the first and second jaws. However these device fail to provide high strength tissue welds or seals. There is a need for a surgical devices that can produce strength tissue welds or seal particularly in larger blood vessels including arteries and veins.

BRIEF SUMMARY OF THE INVENTION

Various embodiments of the invention provide a systems, devices and methods for modulating the application of radiofrequency (Rf) energy application to biological tissue to create high strength thermal welds or seals in targeted tissues. Particular embodiments provide a system and method for performing a "one-step" welding-transecting procedure wherein the surgeon can contemporaneously (i) engage tissue within a jaw structure (ii) apply Rf energy to the tissue, and (iii) transect the tissue.

In one aspect, embodiments of the invention provide an electrosurgical system including a jaw structure configured to apply differential energy levels across jaws engagement surfaces using "smart" materials without the need for complex feedback circuitry coupled to thermocouples or other sensors in the jaw structure. Many embodiments provide a jaw structure that can engage and weld tissue bundles, defined herein as bundles of disparate tissue types (e.g., fat, blood vessels, fascia, etc.). For the welding of tissue bundles, the jaw surfaces are configured to apply differential energy levels to each different tissue type simultaneously.

In another aspect, embodiments of the invention provide system and methods for uniformly heating and welding tissue using the application of Rf energy. In order to create the most effective "weld" in tissue, a targeted volume of tissue is desirably uniformly elevated to the temperature needed to denature proteins therein. To create a "weld" in tissue, collagen, elastin and other protein molecules within an engaged tissue volume are desirably denatured by breaking the inter- and intra-molecular hydrogen bonds—followed by re-crosslinking on thermal relaxation to create a fused-together tissue mass. It can be easily understood that ohmic heating in tissue—if not uniform—can at best create localized spots of truly "welded" tissue. Such a non-uniformly denatured tissue volume still is "coagulated" and will prevent blood flow in small vasculature that contains little pressure. However, such non-uniformly denatured tissue will not create a seal with significant strength (e.g. burst or leak strength, etc), for example in 2 mm. to 10 mm. arteries that contain high pressures. Accordingly, embodiments of the invention utilize positive temperature coefficient of resistance and related materials to sense and respond to temperature in engaged tissue to modulate Rf energy delivery to the engaged tissue to uniformly heat a target tissue volume to in turn produce a uniformly denatured tissue volume and thus, a uniformly welded tissue volume.

In a related aspect, embodiments of the invention provide systems and methods for creating thermal "welds" or "fusion" within native tissue volumes using a combination of energy and force application. The alternative terms of tissue "welding" and tissue "fusion" are used interchangeably herein to describe thermal treatments of a targeted tissue volume that result in a substantially uniform fused-together tissue mass, for example in welding blood vessels that exhibit substantial burst strength immediately post-treatment. The strength of such welds is particularly useful one or more of the following (i) for permanently sealing blood vessels in vessel transection procedures, (ii) for welding organ margins in resection procedures, (iii) for welding other anatomic ducts wherein permanent closure is required, and also (iv) for vessel anastomosis, vessel closure or other procedures that join together anatomic structures or portions thereof. The welding or fusion of tissue as disclosed herein is to be distinguished from "coagulation", "sealing", "hemostasis" and other similar descriptive terms that generally relate to the collapse and occlusion of blood flow within small blood vessels or vascularized tissue. For example, any surface application of thermal energy can cause coagulation or hemostasis—but does not fall into the category of "welding" as the term is used herein. Such surface coagulation does not create a weld that provides any substantial strength in the affected tissue.

At the molecular level, the phenomena of truly "welding" tissue as disclosed herein may not be fully understood. However, the authors have identified the parameters at which tissue welding can be accomplished. An effective "weld" as disclosed herein results from the thermally-induced denaturation of collagen, elastin and other protein molecules in a targeted tissue volume to create a transient liquid or gel-like proteinaceous amalgam. A selected energy density is provided in the targeted tissue to cause hydrothermal breakdown of intra- and intermolecular hydrogen crosslinks in collagen and other proteins. The denatured amalgam is maintained at a selected level of hydration—without desiccation—for a selected time interval which can be very brief. The targeted tissue volume is maintained under a selected very high level of mechanical compression to insure that the unwound strands of the denatured proteins are in close proximity to allow their intertwining and entanglement. Upon thermal relaxation, the intermixed amalgam results in "protein entanglement" as re-crosslinking or renaturation occurs to thereby cause a uniform fused-together mass.

In another aspect, the invention provides an electrosurgical jaw structure that includes a positive temperature coefficient of resistance (PTC or PTCR) body that senses and responds to tissue temperature to thereafter modulate Rf energy application to the engaged tissue. In many embodiments the jaws structure comprises first and second opposing jaws, at least one of which can carry PTCR body. One or both of the jaws includes an energy delivery jaw surface which can be coupled in series to an Rf energy sources such as an Rf generator. The jaw structure can use the PTCR body portions to control the delivery of electrosurgical voltage and current from the Rf energy source to the engaged tissue as well as the current and voltage within the engaged tissue.

In many embodiments, the PTCR body can comprises a matrix comprising PTCR pixels disposed in a field material (i.e., a non pixilated material) such as an electrically insulative polymer material. The jaw structure can be configured to use the PTCR pixels for one or more of the following: i) performing highly localized, pixelated temperature sensing of ohmically heated tissue; ii) controlling current flow in engaged tissue on a highly localized pixelated basis; iii) producing rapid on-off switching of current flow to engaged tissue on a highly localized pixelated basis; and iii) producing highly localized, pixelated Rf current densities in engaged tissue. In various embodiments, the pixel portions can comprise an array wherein each pixel is independently switchable, responsive to the temperature of tissue adjacent each pixel portion, or another tissue property such as resistance, hydration level etc. Also, the array can be configured to produce a substantially uniform thermal effect in tissue including at least one of tissue welding, tissue weld strength, ohmic heating or protein denaturization.

A particular embodiment of the invention provides an electrosurgical working end for performing high strength welding of tissue comprising a body having a tissue contacting surface. The body includes pixel portions and non-pixel portions distributed within the tissue contacting surface. The pixel portions comprise a positive temperature coefficient of resistance (PTCR) material with at least one pixel portion configured to switch Rf current on and off in the at least one pixel portion responsive to tissue temperature adjacent the at least one pixel portion. The pixel portions can be configured to be coupled to an Rf current source such as an Rf generator known in the art. The Rf current source can be coupled to an interior of the body, for example, by doping the body with a conductive coating. Also, the shape of the pixels can be configured to achieve selectable thermal, electrical and/or mechanical properties or a combination properties for the body (e.g. faster pixel switching times, more precise spatial control, etc.)

In an exemplary method of using the above embodiment of the working end and related embodiments, tissue is engaged with the tissue contacting surface of the working end and Rf energy is then delivered to tissue to ohmically heat tissue. Rf current flow to tissue through at least one pixel portion can then be switched or toggled off or one responsive to the temperature of ohmically heated tissue adjacent the at least one pixel portion. This switching can be done on a micron scale so that current flows in one pixel, but is switched off in an adjacent pixel only microns away. On a more macro scale, the switching of current flow can also be utilized to produce a substantially uniform thermal effect in a tissue volume engaged with the tissue contacting surface. This thermal effect can include without limitation, uniform tissue welding, tissue weld strength, ohmic heating, uniform protein denaturization, uniform. Additionally, the switching of current flow can be utilized to create regionalized or pixilated current densities in the engaged tissue which can correlate to the pixel portions.

In some embodiments, the non-pixel portion can have a different or lesser mechanical compressibility than the pixel portions so as to facilitate the gripping or engagement of tissue during the application of force and energy by the working end. The difference in compressibility allows for recesses in the non-pixel portions of the surface to grip the tissue as well as allowing for portions of the surface to dynamically change shape in response to physical changes in the engaged tissue (e.g., shrinkages) as the tissue is heated. This difference in compressibility can also be utilized to maintain minimum hydration levels in tissue during Rf energy delivery by capturing migrating tissue fluid in recesses of the non-pixel portions and hydrating engaged tissue during the delivery of Rf energy using the captured fluid.

DETAILED DESCRIPTION OF THE INVENTION

1. Electrosurgical jaw structure with variable resistive matrices. Various embodiments of the invention provide systems and methods to deliver energy to targeted tissue volumes in a controlled manner to thermally weld or seal targeted tissue. Particular embodiments provide systems and methods for contemporaneously (i) engaging tissue between paired jaws, (ii) delivering energy to the tissue, and (iii) optionally transecting the tissue to provide a "one-step" welding-transecting procedure. Many embodiments provide a jaw structure configured to engage and weld tissue bundles, that is bundles of disparate tissue types (e.g., fat, blood vessels, fascia, etc.). For the welding of tissue bundles, the jaw surfaces can be configured to apply differential energy levels to each different tissue type simultaneously. Related aspects of the invention provide an electrosurgical system that can apply differential energy levels across the jaws engagement surfaces with "smart" materials without the need for complex feedback circuitry coupled to thermocouples or other sensors in the jaw structure.

It has been found that very high compression of engaged tissue in combination with controlled Rf energy delivery is optimal for welding the engaged tissue volume. Additionally, it has been found that ohmic heating and dehydration of tissue in the process of closing the jaw structure greatly assists in the ultimate compression of tissue (particularly tissue bundles) to the desired thickness of a membrane. With the engaged tissue in membrane thickness in a controlled gap between the engagement surfaces of the jaw structure, e.g., from about 0.001" to about 0.05", the method for controlling ohmic heating in tissue can be optimized (as described below).

Figure 1:
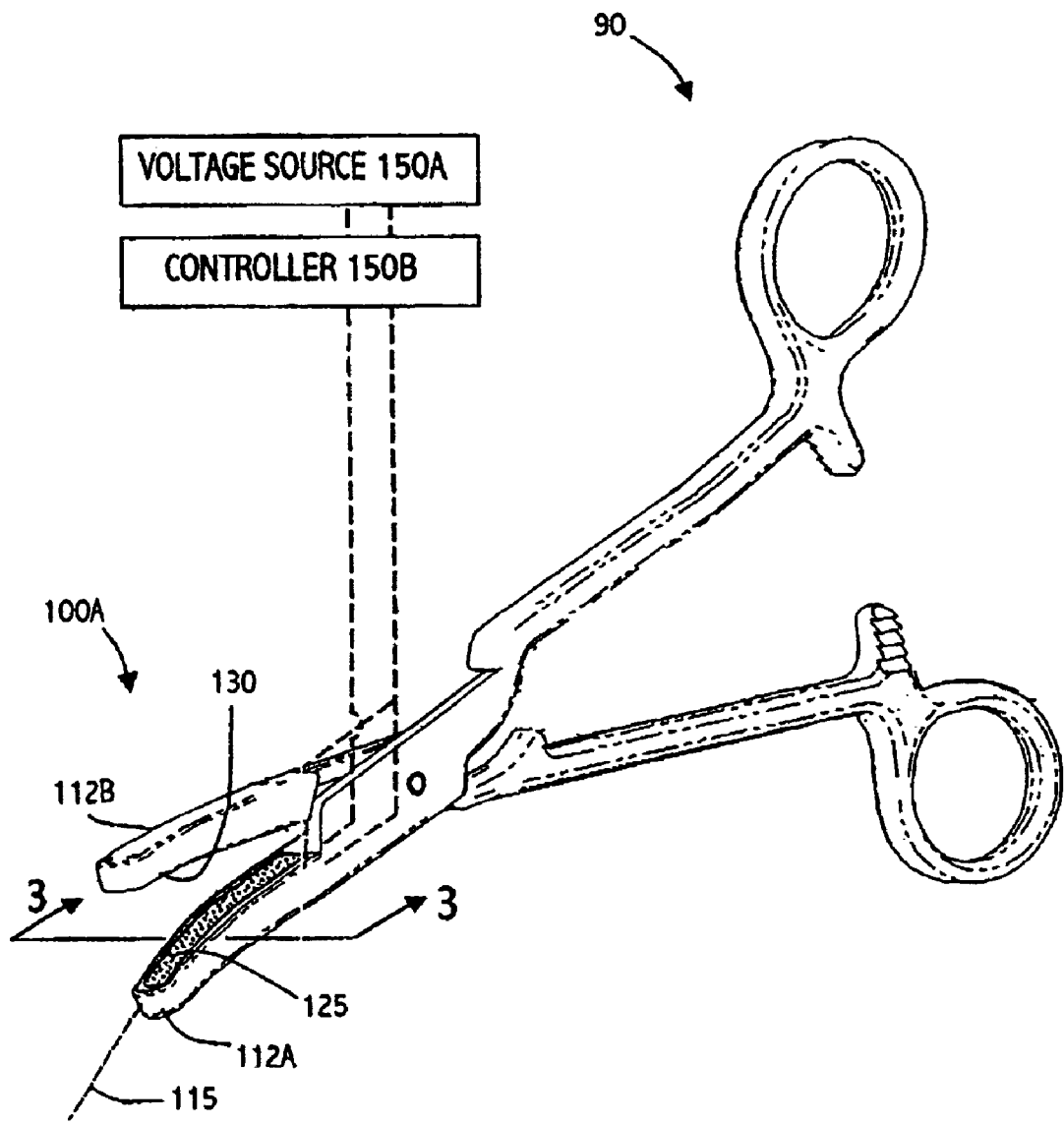
FIG. 1 is a perspective view of an exemplary surgical instrument with and a jaw structure carrying variable resistive matrix bodies for tissue welding corresponding to the invention, the matrix bodies coupled to an Rf source via series and parallel circuits for modulating ohmic heating in engaged tissue.

FIG. 1 illustrates an exemplary forceps-type instrument 90 with a working end or electrosurgical jaw structure 100A corresponding to the invention that comprises first (lower) jaw element 112A and second (upper) jaw element 112B that close or approximate about axis 115 that is straight or curved. It should be appreciated that the jaw elements can be of any curved or straight shape for open or endoscopic surgeries with scissors-type actions or with one or more cam mechanism as is known in the art. The jaws also can carry a sliding cutting blade as will be described below.

Figure 2:
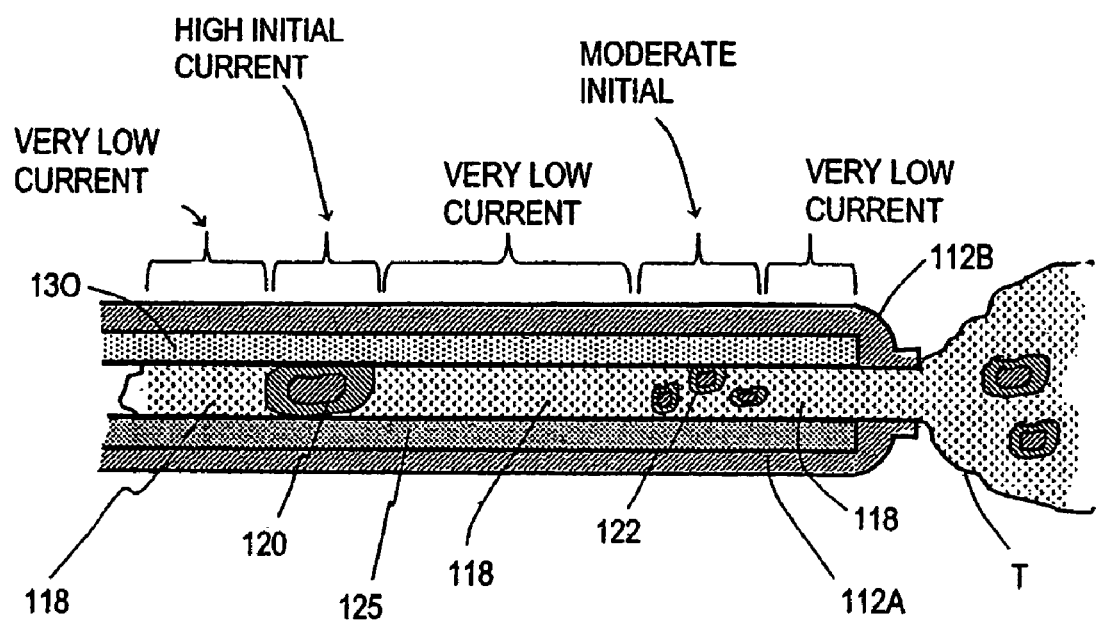
FIG. 2 is a graphic representation of opposing jaws engaging a tissue bundle comprising large blood vessels, fatty tissue and small blood vessels embedded in the fat.

A discussion of the electrosurgical functionality of embodiment of the invention will now be presented. Referring to FIG. 2, the opposing jaws 112A and 112B are depicted schematically as engaging a tissue bundle T of differentiated tissue types—which is a common occurrence in open and endoscopic surgeries. FIG. 2 depicts a longitudinal sectional view of jaws 112A and 112B and an engaged tissue bundle T that contains, for example, insulative fat 118, large blood vessels 120 and smaller embedded blood vessels 122. The gap between the jaws is not-to-scale, and in an actual jaw structure the compressed tissue bundle T could be reduced to the thickness of a thin membrane. In an actual procedure, the tissue bundle would also contain fascia, ligamentous tissues and other tissues that would exhibit a wide range of hydration levels, electrolyte levels etc. that would locally alter tissue impedance, compressibility etc. For convenience, only three tissue types with three impedance levels are shown in FIG. 2, however other tissue types are also contemplated (e.g. bone, tendon, muscle, etc). As indicated graphically by the microcurrents MC in FIG. 2, jaws 112A and 112B can be configured to contemporaneously modulate energy densities across the various types of in the tissue bundle T according to the impedance of each engaged tissue type and region. Further, it is desirable to continuously modulate energy delivery to each tissue type as the region dynamically changes in hydration, impedance and geometry. As energy is delivered, the tissue will shrink as it dehydrates.

Figure 3:
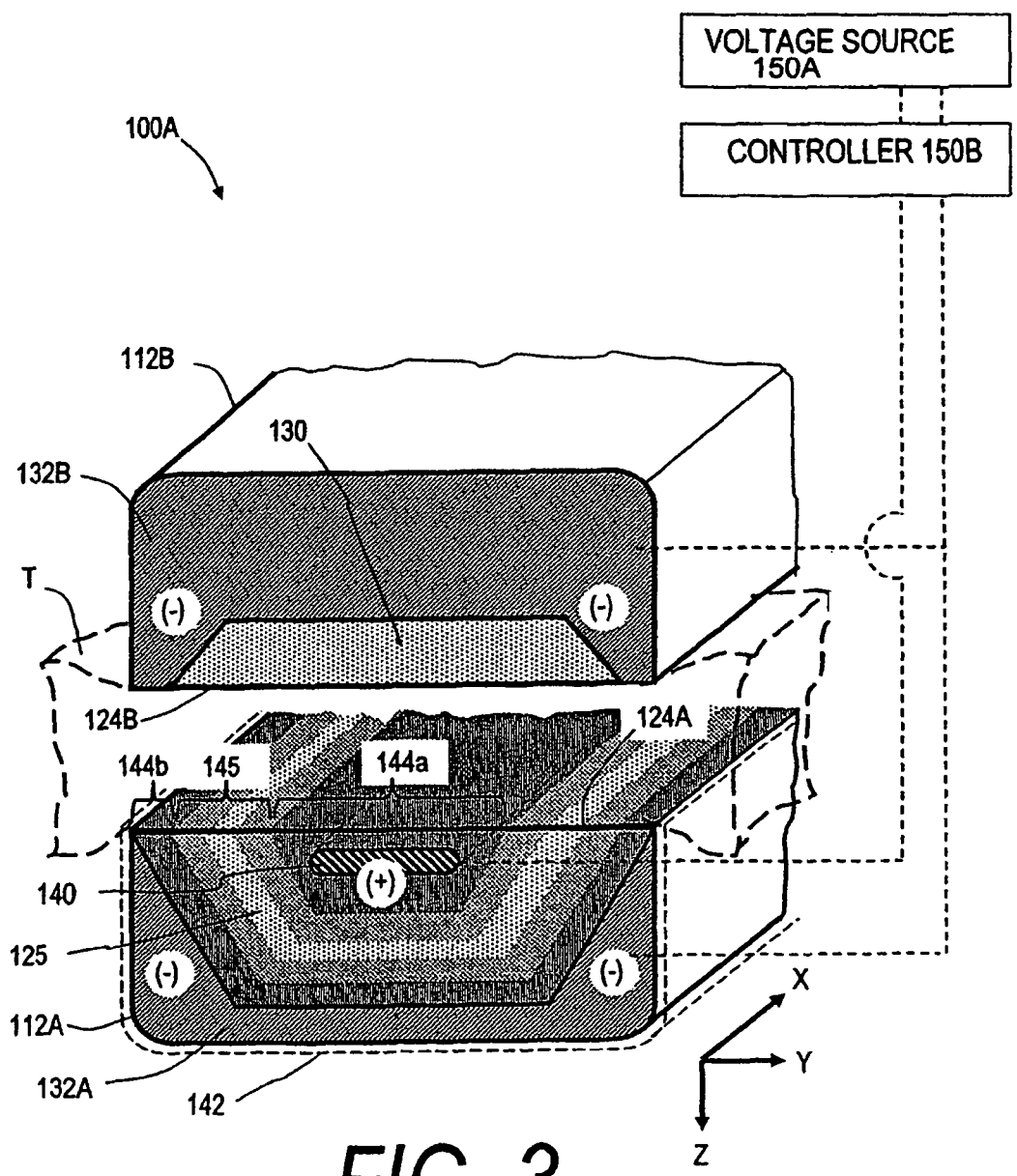
FIG. 3 is a schematic sectional view of the jaw structure of FIG. 1 taken along line 3-3 of FIG. 1 showing the variable resistive matrices in each jaw together with the series and parallel circuits.

FIG. 3 illustrates the tissue-engaging surfaces 124A and 124B of jaws 112A and 112B. Of particular interest, the jaws each carry a three-dimensional (3D) temperature-responsive variable resistive body. The lower jaw 112A carries variable resistive body indicated at 125, also at times referred to herein as a positive temperature coefficient of resistance (PTC or PTCR) body or matrix. By the term three-dimensional, it is meant for example that variable resistive body 125 defines an axial dimension X and a cross-axial dimension Y about the tissue-engaging surface, as well as defining a substantial depth dimension Z that is orthogonal to the plane of the tissue-engaging surface 124A. In other words the variable resistive body or matrix 125 has a selected thickness dimension in preferred embodiments to provide a multiplicity of varied local current flow paths through the matrix as it dynamically responds to adjacent ohmically heated tissue, as will be described below. The upper jaw 112B in one preferred embodiment as in FIG. 3 carries variable resistive body 130 that again can have any suitable depth dimension.

Still referring to FIG. 3, it can be seen that lower jaw 112A has a structural component or body 132A that is of a suitable electrical conductor material so that it functions as an electrode—that is indicated for convenience with a negative polarity (−). Similarly, the upper jaw 112B has structural component or body 132B that is has the same polarity (−) as the lower jaw body. An electrically conductive member or electrode 140 is provided within variable resistive matrix 125 either at the tissue-engaging surface 124A or proximate the surface as depicted in FIG. 3. Both jaws optionally can have an insulative coating indicated at 142 at the exterior of lower jaw 112A.

In a preferred embodiment as in FIGS. 2 and 3, the variable resistive matrices 125 and 130 in lower jaw 112A and upper jaw 112B comprise a polyethylene or a medical grade silicone polymer that is doped with conductive particles (e.g., carbon). The use of such temperature-responsive variable resistive materials is described for related uses in co-pending U.S. patent application Ser. No. 10/351,449 filed Jan. 22, 2003 titled Electrosurgical Instrument and Method of Use; Ser. No. 10/032,867 filed Oct. 22, 2001 titled Electrosurgical Jaw Structure for Controlled Energy Delivery, both of which are incorporated herein by reference. Polymer positive temperature coefficient materials are known in the field of overcurrent protection devices that will trip and become resistive when a selected trip current and temperature is exceeded.

Figure 4A:
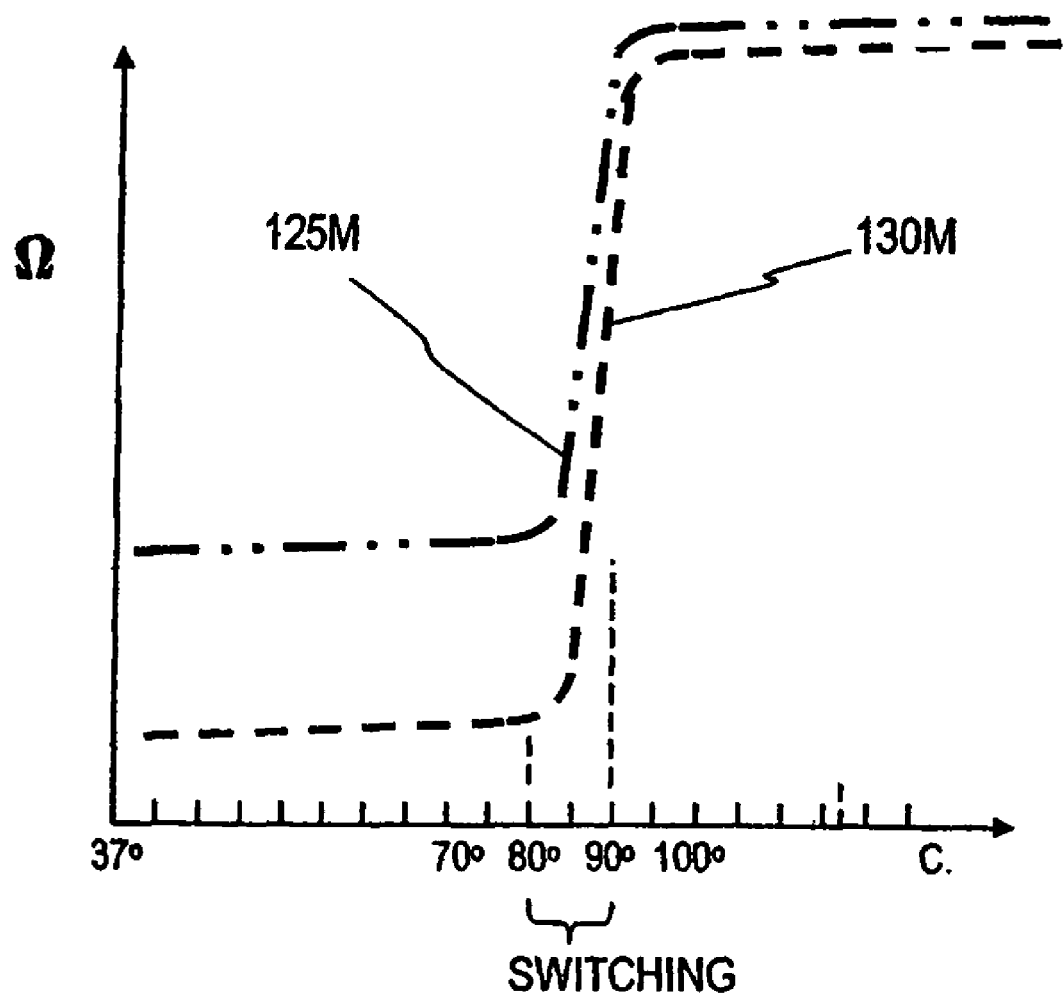
FIG. 4A is a diagram of the temperature-impedance curves of exemplary variable resistive matrix bodies as in FIG. 3.

In general, the temperature-responsive variable resistive materials for use in the invention are fabricated of a non-conductive polymer that exhibits two phases that define greater and lesser conductive states. The first phase is a crystalline or semi-crystalline state where the polymer molecules form long chains and are arranged in a more ordered architecture. When the temperature of the material is elevated, the polymer molecules maintain the crystalline architecture or structure through a selected temperature range. The polymer is designed to transition to an at least partly amorphous phase from the crystalline state at a selected temperature range. In the amorphous state, the molecules are aligned more randomly, and there may be slight changes in material geometry at the macroscale. The non-conductive polymer is combined with a dispersed, highly conductive particles (e.g., carbon micro- or nanoparticles) to form a matrix. In the crystalline phase of the polymer, the carbon particles are packed into the crystalline boundaries and form many conductive paths across and through the matrix material. In this low temperature crystalline state, the polymer-carbon matrix is engineered to have a low resistance. FIG. 4A illustrates the positively-sloped impedance-temperature curve 130M of an exemplary variable resistive matrix 130 of FIG. 3.

In many embodiments, the jaw structure 100A as in FIG. 3 is configured to engage tissue and apply Rf energy to the engaged tissue T to cause ohmic heating therein. After the tissue is elevated in temperature, heat is conducted from the engaged tissue T back to the variable resistive matrices 125 and 130 to thereby elevate temperatures in at least surfaces region of the matrices 125 and 130. Details of the actual method of using the matrices to provide high temperature and low temperature process limits are described below. As long as the temperature increase in the matrix portion adjacent the ohmically heated tissue does not cause a phase change in the polymer, current can flow unimpeded through the matrix. When the temperature of the matrix material is elevated to a selected temperature, called a switching range herein, the temperature will cause a phase change in the polymer (see FIG. 4A). The crystalline structure of the polymer will disappear, the polymer volume will expand, and the carbon chains that allow conduction across the matrix will be broken—resulting in an extraordinary increase in resistance. The polymer-carbon matrix can define a resistance measured in milliohms or ohms before the phase change. After the phase change, the matrix' resistance can be measured in megaohms. Current flow can be reduced accordingly, or terminated, which is used in particular manners corresponding to the invention to precisely control Rf energy densities in the engaged tissue.

The process described above is reversible so that when an affected portion of a matrix falls in temperature, the polymer component will return to its crystalline structure and that particular matrix volume will return its original state. The conductive carbon particles will reform into conductive paths within the interstices of the crystalline polymer architecture. It has been found that the variable resistive body, for example body 130 in the upper jaw, can spatially modulate Rf current flows in a dynamic manner wherein micron scale regions are conductive and adjacent micron scale regions are non-conductive in response to the temperature of engaged tissue.

As the temperature of the matrix falls, it appears that the exact same conductive paths may not exactly reform themselves after first use of the matrix, and for this reason the polymer matrices of the invention may be temperature cycled several times in the fabrication process which appears to cause the material to have substantially resettable conductive paths. In the fabrication process, the matrix can also be treated in various processes (e.g., gamma, UV irradiation etc.) to cross-link the polymer or co-polymers of the matrix.

Figure 4B:
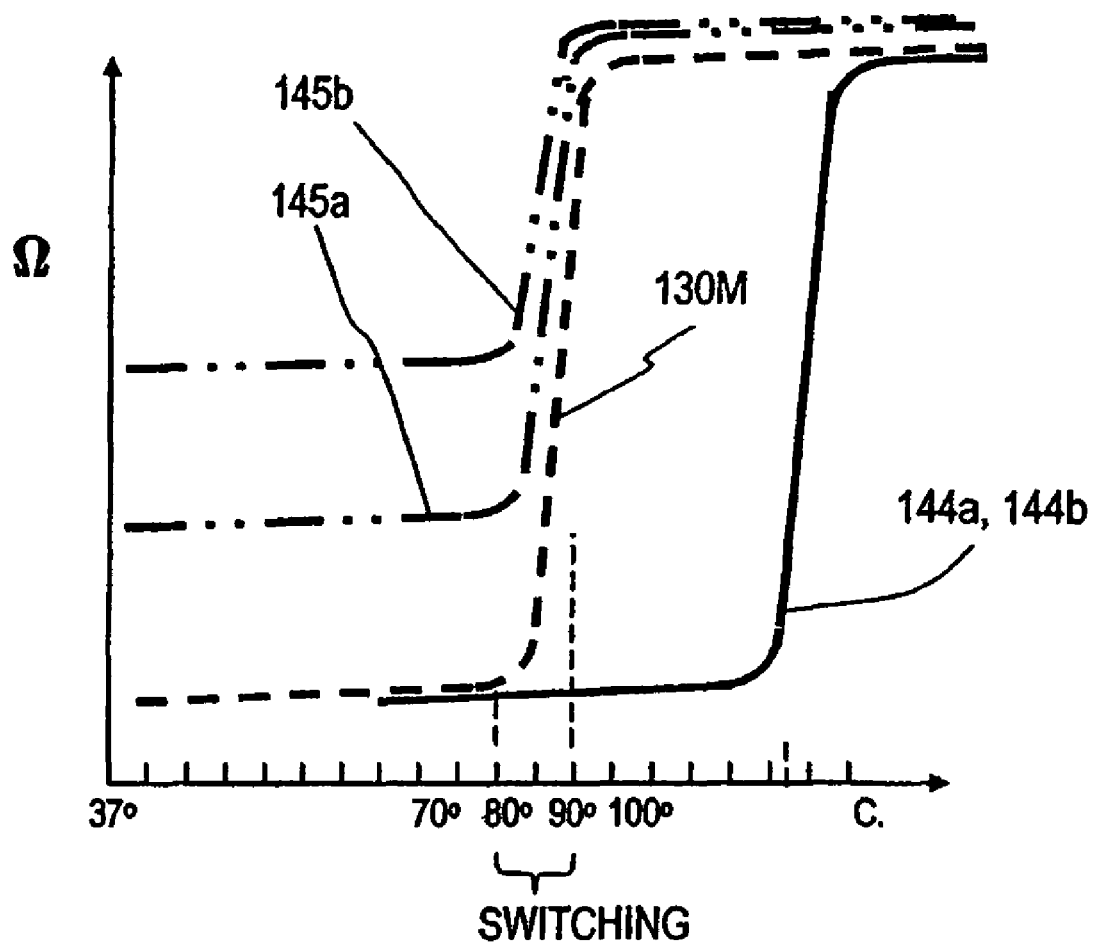
FIG. 4B is a diagram similar to that of FIG. 4A illustrating alternative temperature-impedance curves of variable resistive matrix bodies.

Referring again to FIG. 3, one embodiment of polymer matrix 125 has at least two differentiated regions 144 and 145 that define different temperature-impedance curves as illustrated in FIG. 4B. The regions 144a and 144b (collectively 144) at the center of the lower jaw and the laterally-outward edge of the jaw are of a highly conductive matrix that will only terminate current flow therethrough at a high temperature, for example between 100° C. and 200° C. as shown in FIG. 4B. These regions 144 effectively function as the opposing polarity conductive electrodes as the regions 144 are in contact with the central first polarity conductor 140 and the second polarity jaw body 132A. The lower jaw's matrix region 145 can also provide a plurality of slightly different regions 145a and 145b the have somewhat different base resistances and/or switching ranges as shown in FIG. 4B for reasons described below. In any event, matrix region 145 has a base resistance that somewhat higher than that of matrix 130 in the upper jaw 112B. The jaw structure is coupled to voltage source 150A (a radiofrequency generator) and controller 150B for controlling duration of energy delivery and other Rf parameters (FIG. 3). The manner in which matrices 125 and 130 operate to modulate energy densities in tissue will be described in greater detail below.

Figure 5:
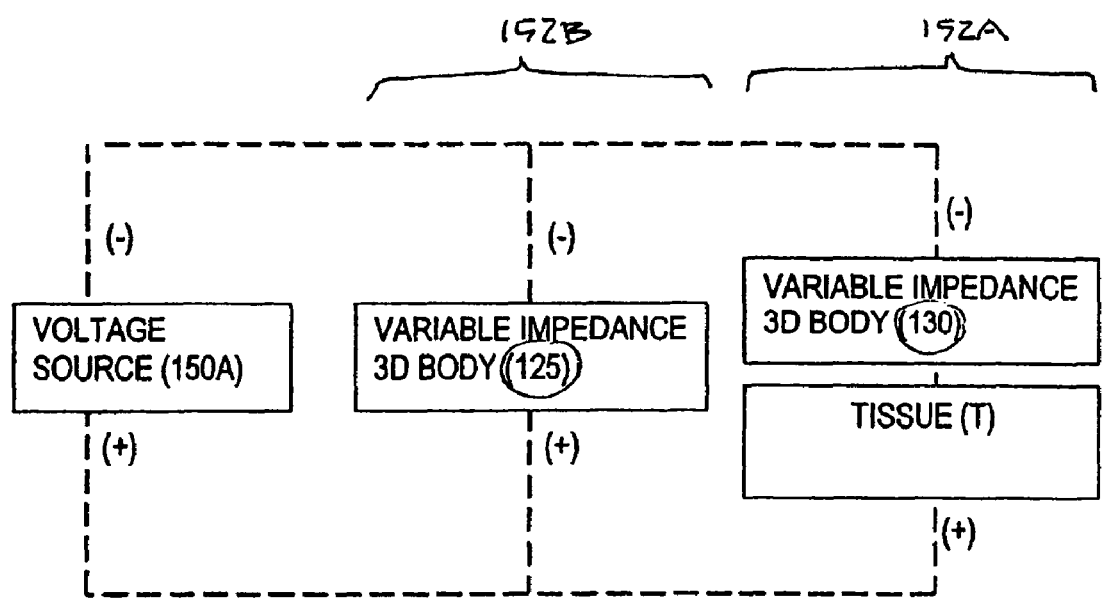
FIG. 5 is a block diagram of the series and parallel electrical circuit components of the working end of FIG. 3.

Of particular interest, the jaw structure 100A corresponding to the invention utilized the two differently performing matrices 125 and 130 (FIG. 3) in combination with the series and parallel circuitry of FIG. 5 to provide effective high and low process limits for temperatures and energy densities in the engaged tissue T. It has been found that such dynamic energy and temperature controls are optimal for creating uniform thermal effects in tissue to denature tissue proteins and to create high strength welds. In one embodiment as in FIG. 3, the matrix 130 in upper jaw 112B is engineered to exhibit unique temperature-impedance characteristics represented by the positively-sloped curve 130M of FIG. 4B. This matrix 130 maintains a relatively low base resistance over a selected base temperature range with a dramatically increases resistance above a selected narrow temperature range (switching range) that can be any 1° to 10° range between about 50° C. and 200° C., and more preferably between about 70° C. and 120° C. In comparison, the matrix region 145 in lower jaw 112A is designed to have an impedance-resistance curve exhibiting a higher initial base resistance (see FIG. 4B). The matrix region 145 provides this higher base resistance over a similar temperature range as matrix 130. The matrix 145 and its temperature-impedance curves (145a, 145b) in FIG. 4B again exhibits a dramatically increasing resistance above its selected switching range, which can fall in the range described previously with reference to matrix 130.

Figure 6A:
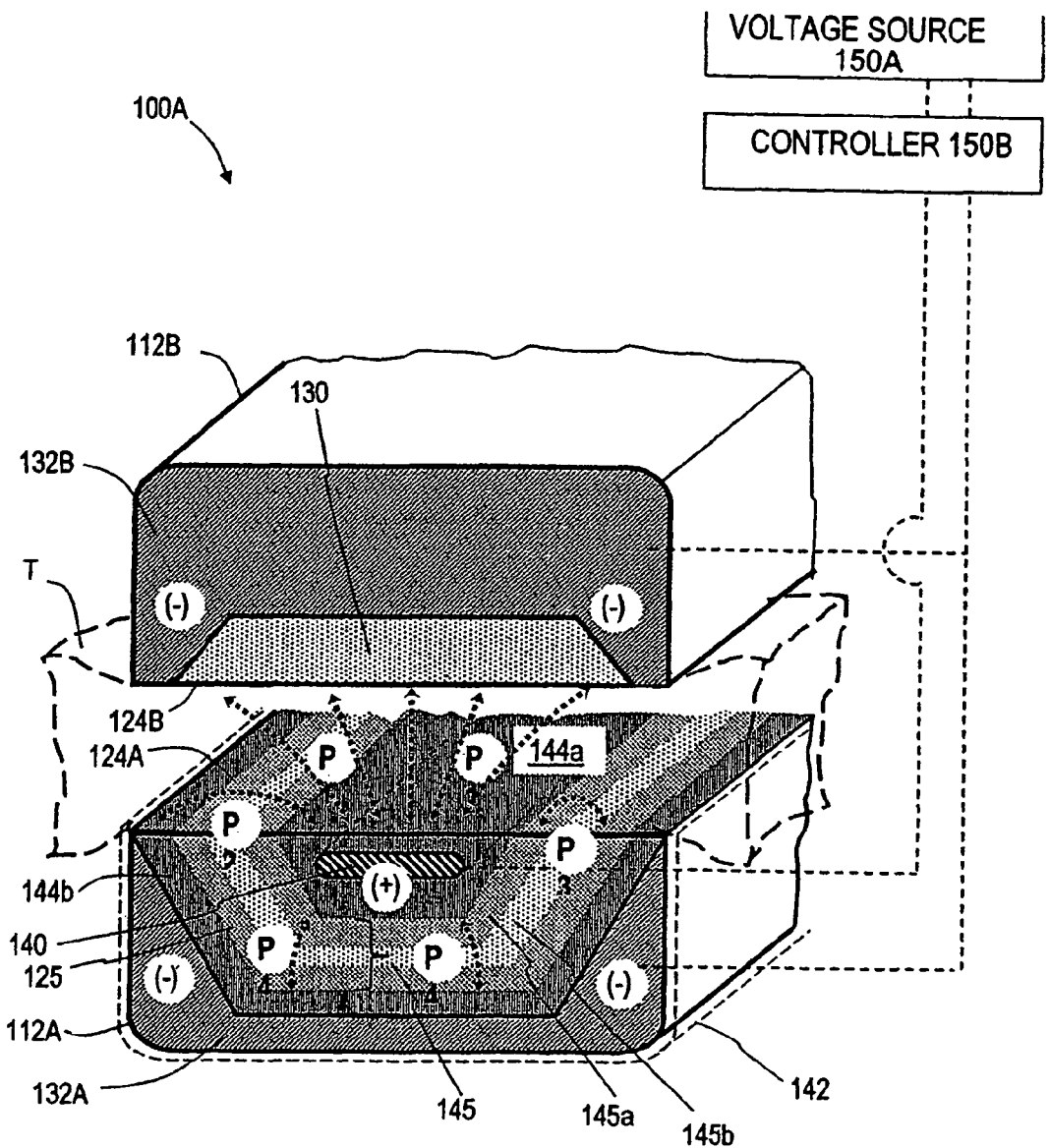
FIG. 6A is a sectional schematic view of the variable resistive matrix bodies showing potential current flow paths in the engaged tissue and the matrix bodies.

FIG. 6A schematically depicts the manner in which the jaw structure 100A of FIGS. 1 and 3 can self-modulate current flow among multiple paths—depending on the temperature of the engaged tissue and other electrical conduction parameters of the tissue to which the matrices 125 and 130 respond. FIG. 6A depicts a sectional view of the jaws 112A and 112B as in FIG. 3 engaging tissue T in phantom view. In FIG. 6A, the tissue thickness is not to scale to allow a graphic representation of potential current paths. In actual operation, the working end 100A of FIG. 6A has the ability to modulate current flow among multiple different paths through the tissue T as well as through the matrices 125 and 130. Current and voltage in the tissue T is modulated after the tissue is ohmically heated—and thereafter the tissue T transfers heat by passive conduction to adjacent regions of matrices 125 and 130. While there will exist a multiplicity of potential current paths in the engaged tissue and matrices, FIG. 6A, and FIGS. 10A-10D in a simplified jaw, illustrate four generally different flow paths, P1 through P4, that effectively describe the general types of current flow paths that come into play in the self-modulating Rf ohmic heating method of the invention. The flow paths P1 through P4 do not indicate that current flows are dynamic and can be localized (conductive or non-conductive) across micron scale regions of the engagement surface of the matrices. The timing and potential switching between current paths during operation is described in more detail below.

Figure 6B:
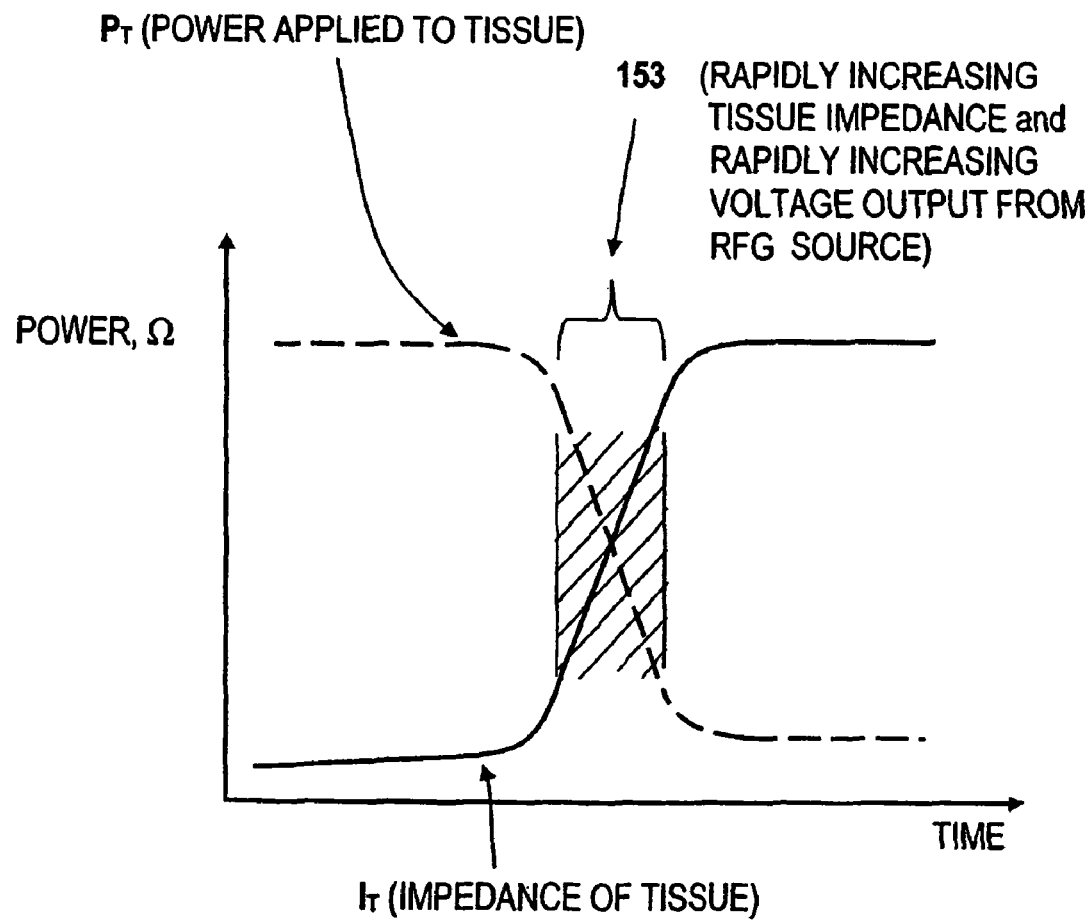
FIG. 6B is a graph illustrating power and impedance curves that illustrates feature of the invention.

Further, FIG. 6B graphically depicts important operational characteristics of the method corresponding to the invention, wherein Rf energy application to the engaged tissue is illustrated over a selected time interval. The horizontal axis indicates elapsed "time" after initiation of Rf energy delivery and ohmic heating, while the vertical axis indicates impedance ($\Omega$) or power (P) for various curves. The curve marked $I_T$ represents the impedance of the engaged tissue over time. The curve marked $P_T$ represents the power (function of voltage and current) that is applied to the engaged tissue over time. As can be seen in FIG. 6B, after tissue is initially engages and Rf energy is applied, the impedance of the tissue ($I_T$) remains low at a base level for an initial period, and power applied ($P_T$)

to the engaged tissue is high for the corresponding time interval. In terms of schematic current flow paths in tissue, this initial rapid, high power ohmic tissue heating is generally represented by flow paths $P_1$ (and to some extent path $P_2$) in FIG. 6A. In other words, substantial RF energy densities are created in the tissue as current flows between electrode 140 and opposing jaw body 132B through the multiplicity of conductive paths in the variable resistive body 130. In terms of the circuitry of the working end, referring to FIG. 5, the high current flow occurs in the (first) series component indicated at 152A that engages the tissue. It is during this time interval, that may be only a fraction of a second to several seconds, that the temperature-responsive variable resistive body 130 in the upper jaw plays its major current limiting role in spatially modulating Rf paths in the highly compressed tissue to cause uniform ohmic heating over the engagement surfaces and within adjacent tissue regions.

Referring back to FIG. 6B, as the tissue impedance rises in curve $I_T$, a critical time interval in reached (indicated at 153; hatched area) wherein tissue desiccation and potential arcing is possible—which would cause potential tissue carbonization and destroy, reduce or eliminate weld strength. In the prior art, the commercially available Rf devices with feedback power control typically fail and cause tissue desiccation and charring. The feedback mechanisms, such as a thermocouple or impedance monitoring, cannot respond rapidly and cannot provide a spatial response to direct current flow away from only the desiccated tissue. At the same time that tissue impedance rises, there is a rapid increase in voltage output from the generating source in this initial period after the source 150A is turned on. It is at this time that the temperature-responsive variable resistive body 125 in the lower jaw 112A plays its voltage or power limiting role to prevent potential arcs in the lowered-impedance tissue. The potential arcs in the tissue would occur principally in flow path $P_2$ (and related path $P_3$) wherein opposing polarity conductive portions are in closest proximity. The objective of the engagement surface and circuitry is to automatically limit power—to insure that an arc does not occur. In various embodiments, this is accomplished by the variable resistive body 125 in lower jaw 112A to allow current to flow in paths $P_4$ directly between the opposing polarity body portions at an interior region of the jaw—and not within the tissue. In terms of the circuitry of the working end, referring again to FIG. 5, this subsequent current flow for prevention of arcs occurs in the (second) parallel component indicated at 152B. It can easily be understood that current flow is then modulated between the first and second circuit components 152A and 152B (FIG. 5) which, in turn, depends on the temperature (and hence impedance) of variable resistive body 130 (see FIG. 5) in the first circuit component 152A. Referring back to FIG. 6B, it can be seen that the power-to-tissue curve ($P_T$) drops to a low level when the tissue is welded since the energy is directed through the second circuit component 152B (FIG. 5). It should be appreciated that the power and impedance curves of FIG. 6B are a graphic generalization, and each micron scale region tissue would be represented by an independent set of power and impedance curves at any instant in time. For example, FIG. 10D illustrates that different spaced apart regions of engagement surfaces modulate current flow differently—depending on highly localized temperature and compression parameters of the engaged tissue.

In FIG. 6A, flow paths P1 indicates potential Rf microcurrent flows directly through tissue T between first polarity electrode 140 and conductive region 145 and the low resistance matrix 130 of upper jaw 112B that overlies the (opposing) second polarity jaw body 132B. It can be understood that these current paths P1 provide initial rapid ohmic heating of tissue. Flow paths P2 indicate Rf current flow through tissue T between the highly conductive regions 144a and 144b that are laterally spaced apart in the lower jaw that are in contact with first polarity conductor 140 and second polarity jaw body 132A, respectively.

Of particular interest, potential current flow paths indicated at P3 and P4 are unique to the invention and come operate to modulate ohmic heating in engaged tissue as its conductive parameters (impedance, temperature, and hydration) are dynamic during energy application. Potential flow paths P3 represent potential microcurrent paths through a region of tissue between spaced apart surface portions of matrix 125 that engage such a tissue region. Potential current flow paths P4 are at an interior of the jaw and the 3D matrix 125 wherein current can flow for voltage limiting purposes from electrode 140 across the matrix region 145 to the interior of the opposing polarity jaw body 132A. A more detailed step-by-step description of current flow modulation is provided below in the text accompanying FIGS. 10A-10D.

For clarity of explanation, FIG. 6A depicts the principles of the working end in a basic forceps-type jaw structure 100A of FIGS. 1 and 3. It should be appreciated that the same variable resistive matrices 125 and 130 can be provided in a jaw structure indicated at 100B in FIGS. 7 and 8 that carries a blade for transecting the welded tissue. Further, the same variable resistive matrices 125 and 130 can be carried in a one-step jaw structure that is described below (FIGS. 11-12) wherein jaw closing, Rf energy delivery and tissue transection occur in a single operation. Now referring to FIGS. 7 and 8, a forceps-type instrument is shown with a detachable cartridge 154 that carries a thin flexible blade member 155 that can be pushed by thumb slider 156 when the jaws are locked in a closed position. Such a blade cartridge was disclosed in co-pending U.S. patent application Ser. No. 10/443,974, filed May 22, 2003 titled Electrosurgical Working End with Replaceable Cartridges which is incorporated herein by this reference.

Figure 7:
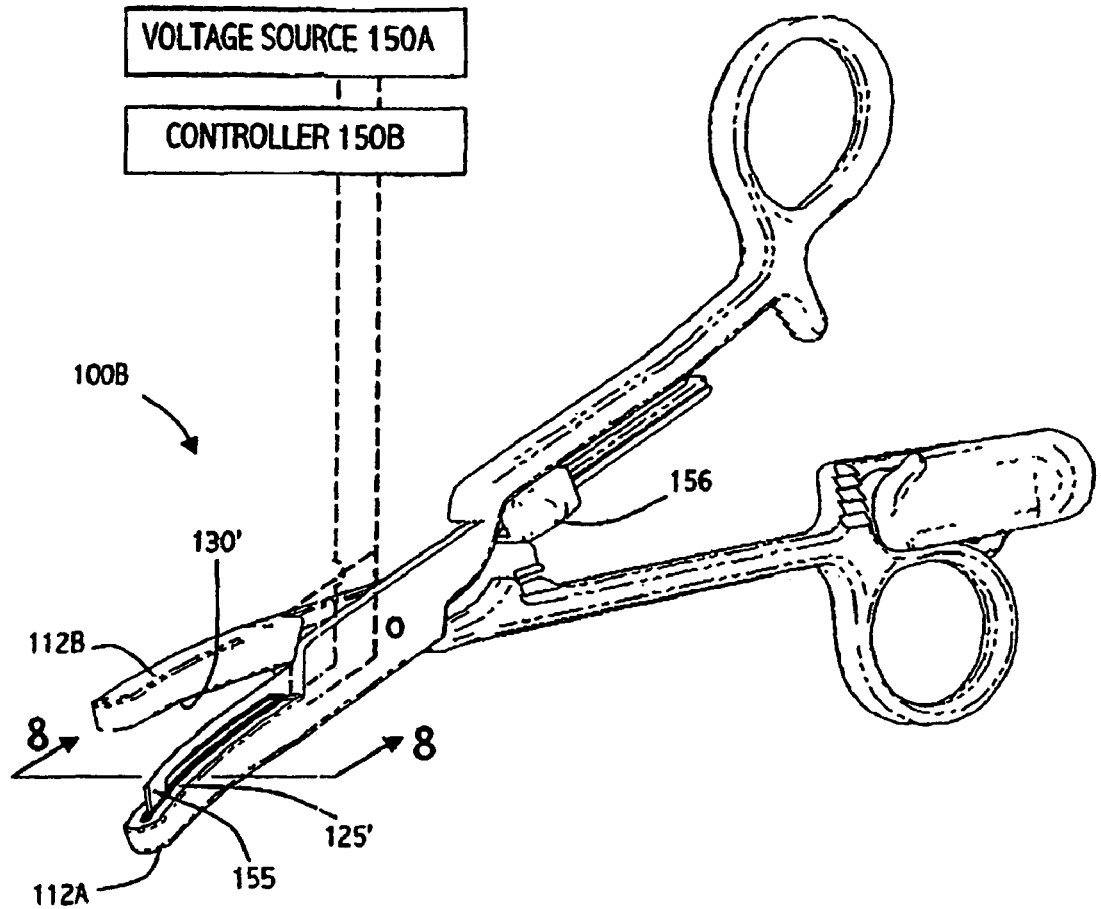
FIG. 7 is a perspective view of an alternative instrument with and a jaw structure carrying variable resistive matrix bodies together with blade means for transecting tissue.
Figure 8:
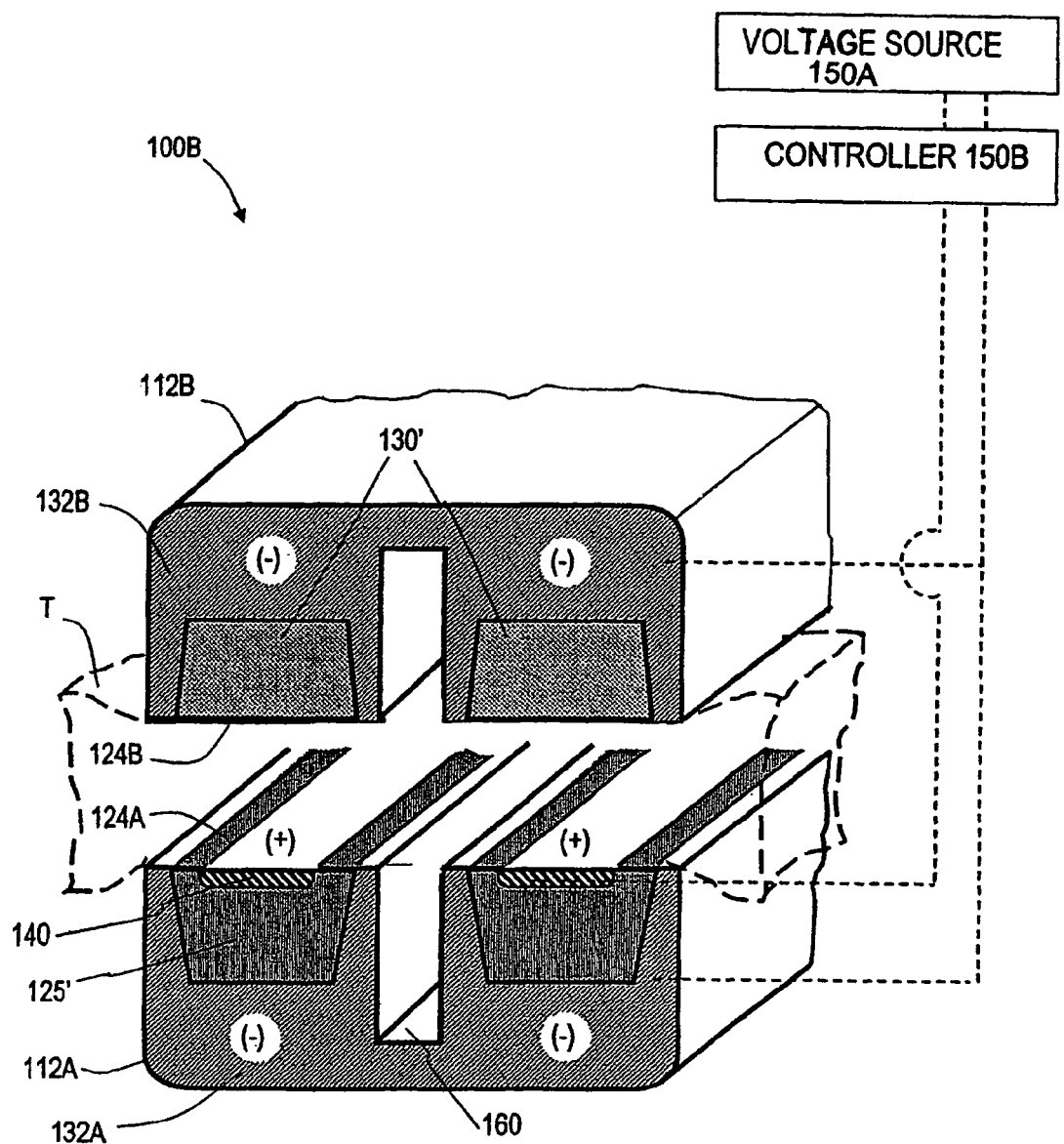
FIG. 8 is a sectional view of the jaw structure of FIG. 7 taken along line 8-8 of FIG. 7 showing the variable resistive matrices in each jaw together blade means.

FIG. 8 illustrates a cross section of the upper and lower jaws 112A and 112B with a central blade slot 160 for receiving the slidable, flexible blade member 155. On either side of the blade slot 160, the jaw bodies carry variable resistive matrices 125' and 130' that are similar (or identical) to the matrices depicted in FIG. 3. In the exemplary embodiment of FIG. 8, the lower jaw 112B has a matrix 125' that is simplified in that electrode 140 is exposed in the center of the jaw's engagement surface 124A with a portion of the 3D matrix 125' extending laterally on either side of blade slot 160 as well as within the interior of the jaw. As can be seen in FIG. 7, matrix extends in a "U"-shape around the end of blade slot 160 to allow welding of engaged tissue around the end of a welded and transected tissue region.

Figure 9:
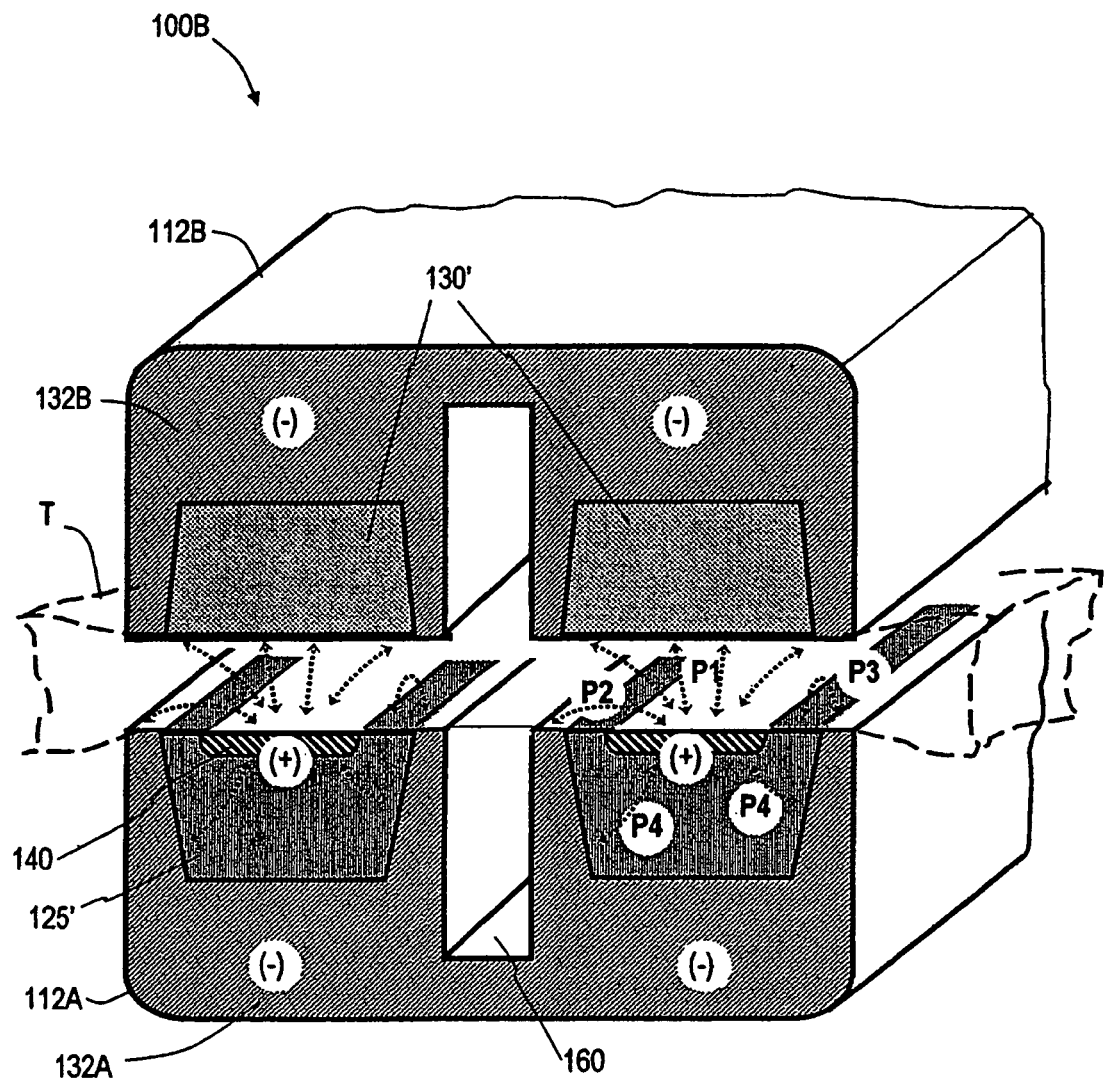
FIG. 9 is a sectional schematic view of the jaw structure of FIGS. 7-8 that illustrates potential current flow paths in the engaged tissue and the matrix bodies.

In all respects, the working end 100B of FIGS. 7-8 functions to modulate Rf energy application to tissue in between multiple potential paths as described above and depicted in FIG. 6A. FIG. 9 illustrates the working end 100B of FIGS. 7-8 and again graphically depicts the potential Rf current paths in tissue and across regions of the variable resistive matrices. The current paths P1, P2 and P3 again represent potential paths in the engaged tissue T. In FIG. 9, the current paths P4 represent paths within the interior regions of matrix 125' between first polarity (+) surface conductor 140 and a second polarity (−) region of jaw body 132A.

2. Method of utilizing temperature responsive variable resistive matrices for Rf modulation. Now turning to FIGS. 10A-10D, the sequential energy delivery phases of the method of the invention is graphically illustrated. In FIGS.

10A-10D, the opposing jaws 112A and 112B are depicted engaging a tissue bundle T, and Rf energy application to tissue is modulated by matrices 125 and 130 between various paths P1-P4 in the tissue to create a uniform temperature without desiccation or charring to provide an effective high strength weld. FIGS. 10A-10D illustrate a basic jaw structure 100C similar to that of FIG. without a blade member, but it should be appreciated that a jaw 100B with a reciprocal blade as in FIGS. 7-8 would create a weld by the same means of energy application and modulation. For clarity of explanation, the engagement surface 124A of FIGS. 10A-10D has the central conductive member or electrode 140 exposed in the surface (cf. FIGS. 7-9).

Figure 10A:
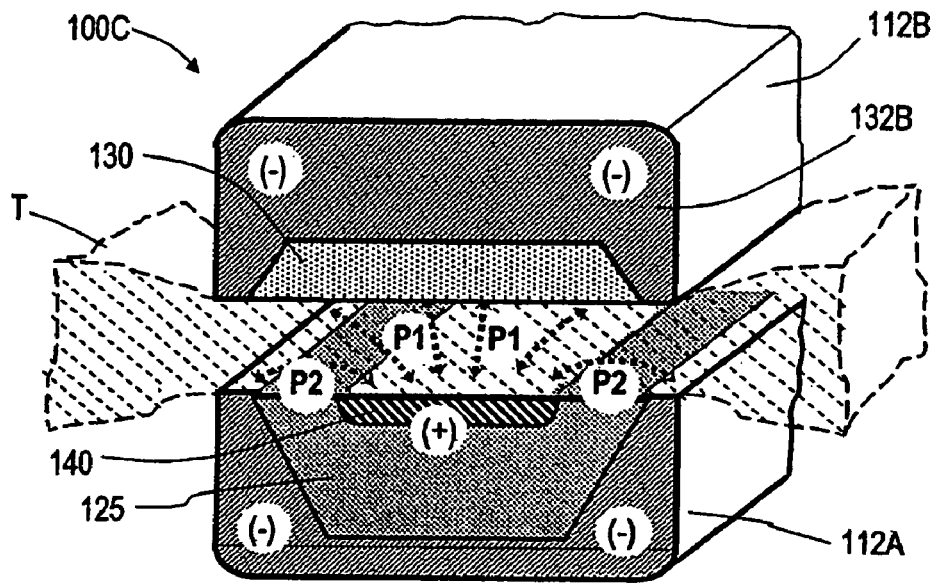
FIG. 10A is a sectional view of the jaw structure of FIGS. 7-8 illustrating an initial step in a method of the invention wherein Rf current flow paths cross the engaged tissue to cause ohmic heating therein.

Turning now to FIG. 10A, an initial energy application step is illustrated wherein tissue bundle T is engaged as the jaws apply compression and the surgeon applies Rf energy to the tissue. At initiation of Rf energy application, FIG. 10A illustrates that current flows are substantially through the tissue between the first polarity conductor 140 and the opposing matrix 130 and laterally-outward upper jaw 132B as well as to the second polarity lower jaw body 132A, that is in paths P1 and P2 as depicted in FIGS. 3 and 9. Thus, FIG. 10A depicts current flow that causes very high energy densities and very rapid ohmic heating in the engaged tissue T. In this initial phase of Rf energy application to the jaw structure 100C and to the engaged tissue T, the matrices 125 and 130 are, in effect, in a stand-by mode and are not yet operating to modulate flow paths of the microcurrents in the tissue. The matrix 130 in the upper jaw at ambient room temperature has a low base resistance (see FIG. 4B) and allows a multiplicity of conductive flow paths all across and through the matrix 130 to the second polarity jaw body 132B from the first polarity conductor 140 in the lower jaw through the tissue T.

In FIG. 10A, the ohmically heated tissue causes conductive heat transfer to the matrices 125 and 130 to heat at least the surface regions of both matrices. At the same time (see FIG. 10B) the ohmically heated tissue T dehydrates, changes its geometry by shrinking and exhibits an increased impedance. In this phase of energy application, the variable resistive matrix 130 responds according to its selected temperature-impedance curve (see FIG. 4B) wherein the material regulate and modulate flow paths P1 of microcurrents therethrough. For example, the switching range of the matrix can be between about 60° C. to 120° C. and is more preferably in the 70° C. to 90° C., range. During and following this phase, the impedance of tissue regions will be substantially matched by the induced impedance of adjacent regions of matrix 130, to thereby modulate current flow in paths P1 between the jaws. At the same time, the matrix 130 will prevent any possibility of arcs or sparks at the interface of jaw surfaces 124A and 124B with the engaged tissue since current flow will be eliminated before excessive high temperatures are reached about any region of the tissue-jaw interfaces. The prevention of such arcs eliminates the possibility of unwanted tissue charring.

During this initial energy application phase, the ohmically heated tissue also will conduct heat back to matrix 125 in the lower jaw 112A to elevate the lower matrix above its selected switching range, for example in the 70° C. to 90° C., range. Still referring to FIG. 10A, as the thickness of tissue T is reduced by compression and ohmic-induced dehydration, the increased impedance of the tissue will first prevent microcurrent flows in paths P1 as the upper jaw's matrix 130 is masked. At this point, there will remain the possibility of microcurrent flows in paths P2 between the electrode 140 and the laterally-outward jaw body portion 132A.

Figure 10B:
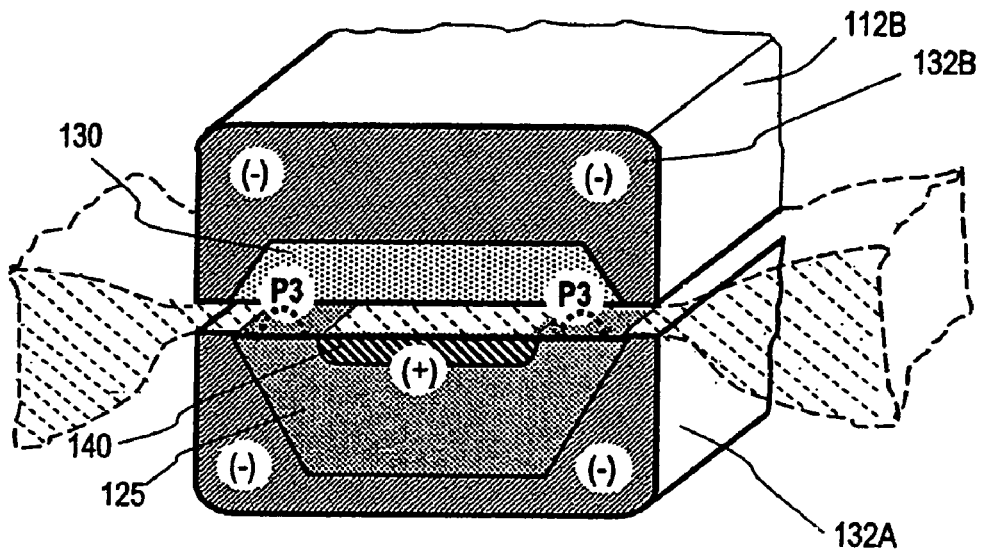
FIG. 10B is a sectional view of the jaw structure of FIG. 10A depicting a subsequent step in a method of the invention with modulated Rf current flow paths in the engaged tissue.

Now referring to FIG. 10B, it can be seen that the dehydrated tissue T typically will be compressed to a thin membrane which can increase its impedance in the most direct paths of current (P1 and P2) between the opposing polarity body portions. With the tissue in this condition, the reduction or termination of ohmic heating will cause slight cooling of the tissue and re-hydration of the tissue can occur due to inward fluid migration. In this state, the lower matrix 125 will respond by cooling and then by causing microcurrent flows in paths P3 as indicated in FIG. 10B. Of particular interest, the increase in ohmic heating is then localized is these lateral regions of the engaged tissue while the tissue impedance still masks the upper jaw matrix 130. During this regulated phase of Rf energy application, the engaged tissue may hydrates to allow current flows in paths P1 and P2 to cause additional ohmic tissue heating. Thus, it can be understood how the temperature responsive matrices will self-modulate ohmic energy densities in the tissue between the various potential flow paths.

Figure 10C:
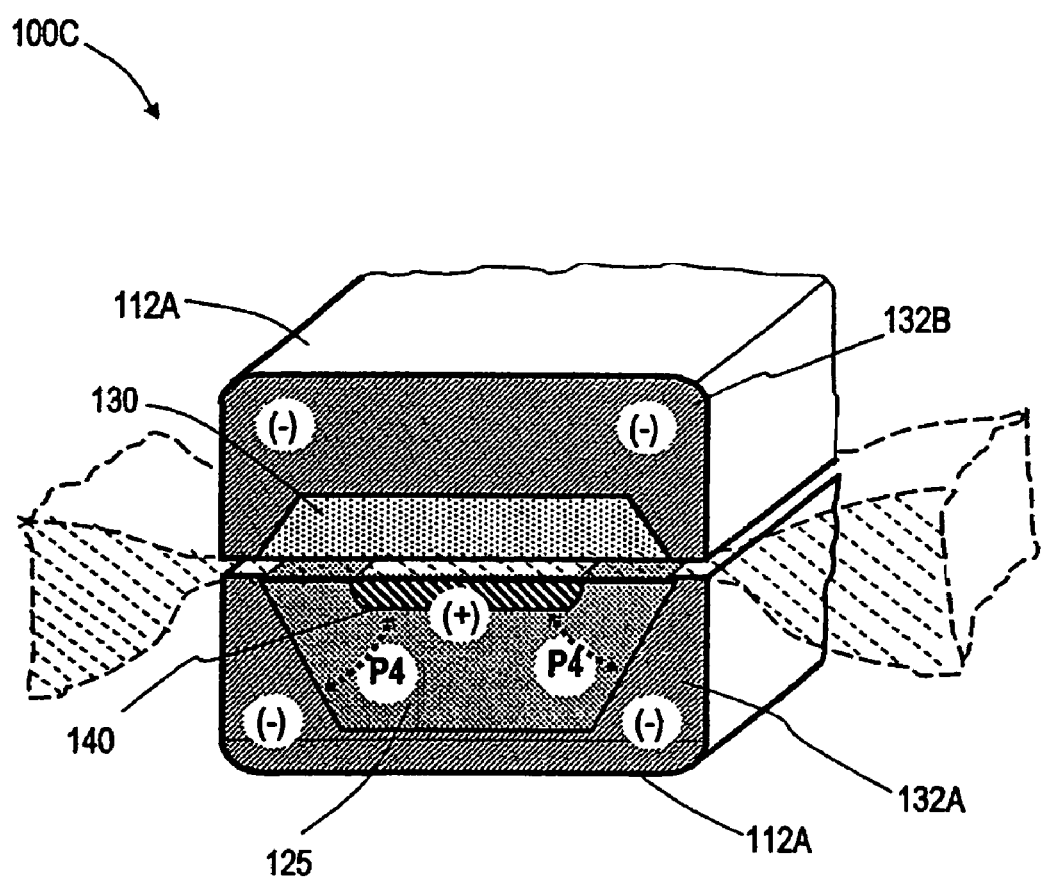
FIG. 10C is another sectional view similar to FIGS. 10A-10B depicting a step in a method of the invention wherein Rf current flow paths within an interior of a variable resistive matrix prevent sparking at a jaw engagement surface.
Figure 10D:
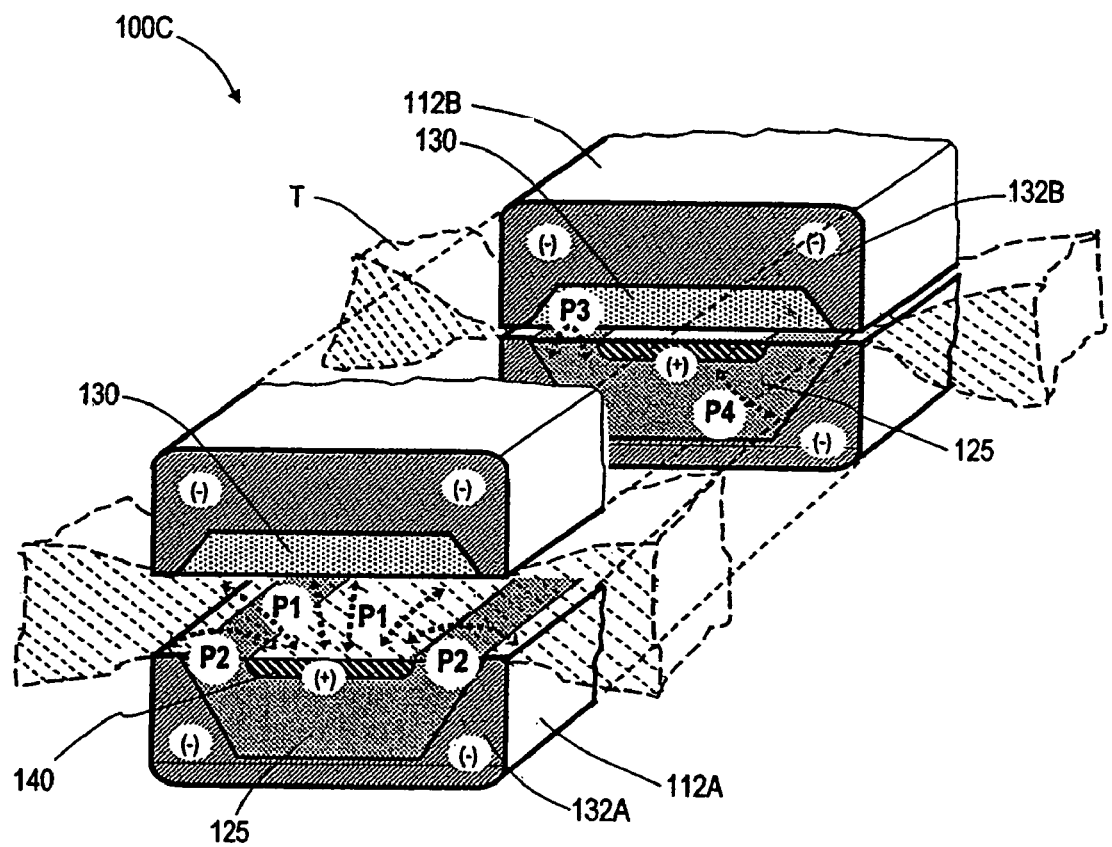
FIG. 10D is another view similar to FIGS. 10A-10C depicting a step in a method of the invention wherein Rf current flow paths occur in different axial regions of the jaws depending on local jaw compression.

FIG. 10C indicates another potential flow path P4 that can come into play if any voltage occurs that could cause an arc at the jaw-tissue interface. In effect, the energy can be dissipated by energy flows in the paths indicated at P4 between the first polarity conductor 140 and the second polarity lower jaw body 132A directly through the lower matrix 125 at the jaw's interior.

FIGS. 10A-10C indicate generally how the temperature-responsive matrices 125 and 130, at the tissue-engaging surfaces 124A and 124B, will modulate ohmic heating in the engaged adjacent tissue T. It should be appreciated that the energy modulation also occurs about very localized regions of the engaged tissue T that is made up of different tissue types as discussed in the text accompanying FIG. 2. Thus as any local region of tissue impedance changes during ohmic heating, the local adjacent region of matrix 130 in the initial phase will move to an impedance matching level.

Further, as described above, the tissue dimension and geometry between the engagement surfaces 124A and 125B of the jaws is dynamic and shrinking during ohmic heating of the tissue T. Thus, the local dynamics of ohmic heating in tissue along the axial length of the jaw can be significant. FIG. 10D illustrates the pivoting jaw structure 100C as applying higher compression to more proximal tissue regions and the jaws close and the tissue dehydrates and shrinks during energy delivery. It can be understood that ohmic heating is thus modulated by matrices 125 and 130 in the jaws' engagement surfaces to provide locally independent energy densities in discrete tissue regions depending on local tissue temperature and impedance—as well as tissue geometry.

It has been found that the system described above can be operated with a pre-set duration of Rf energy delivery, wherein energy flow and tissue heating is self-regulated by matrices 125 and 130 to effectively provide high and low process limits for the selected duration of energy application. Depending on selected power levels and selected matrix parameters, duration of energy application to create an effective weld can range between about 1 second and 20 seconds, and more preferably is between about 3 second and 15 seconds.

Figure 11:
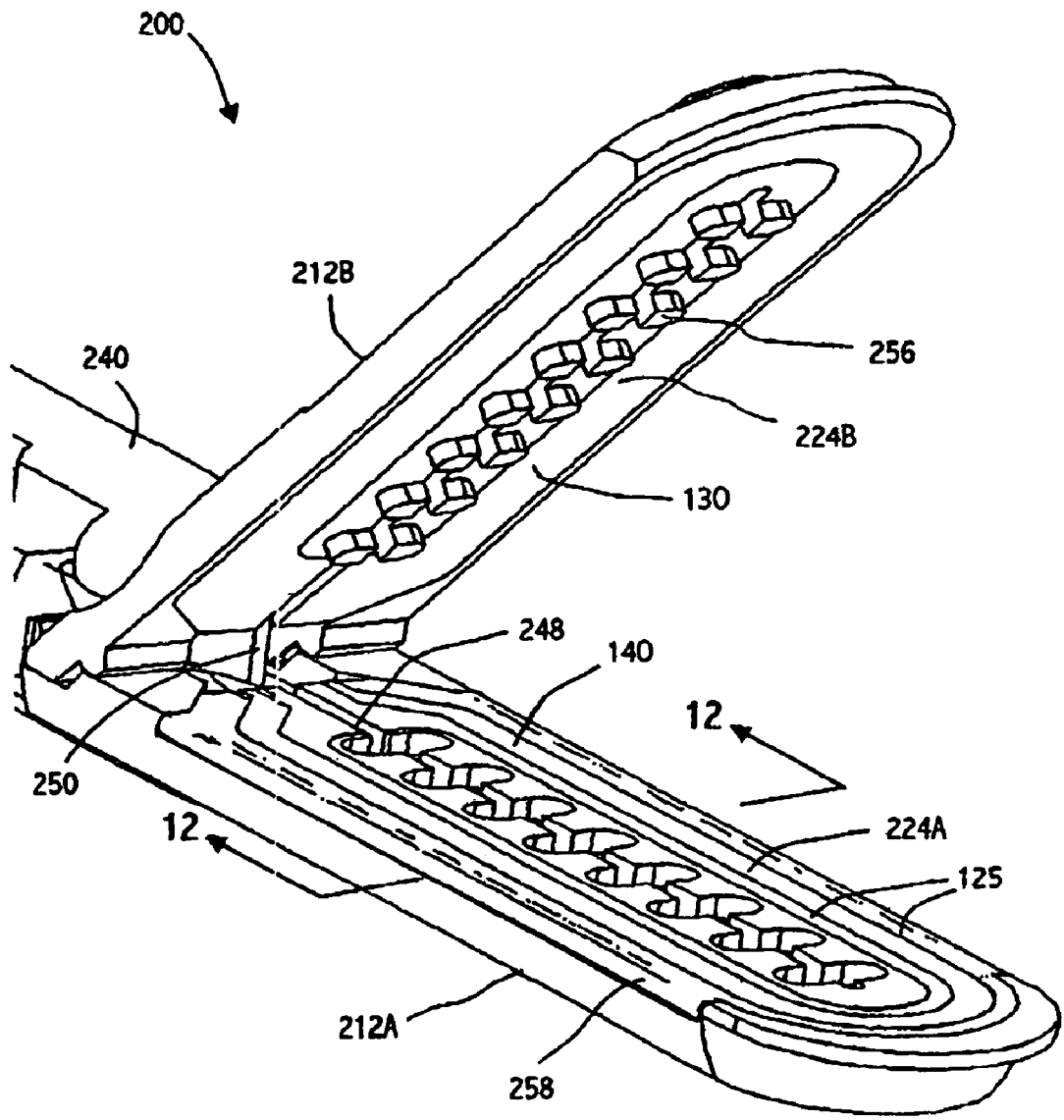
FIG. 11 is a perspective view of an alternative high-compression jaw structure carrying 3D variable resistive matrix bodies that is adapted for one-step tissue welding and transection corresponding to the invention, the matrix bodies coupled to an Rf source via series and parallel circuits.
Figure 12:
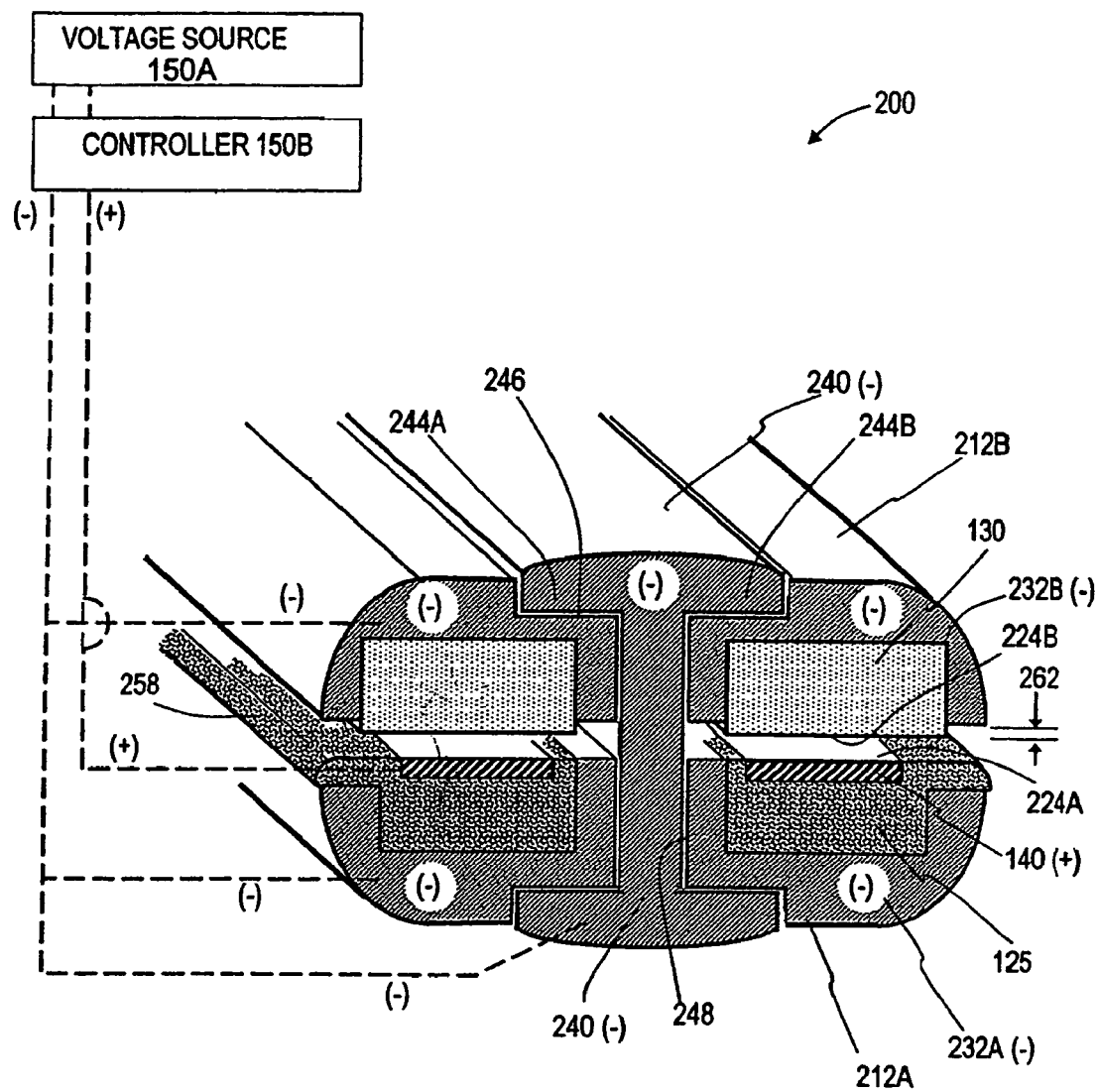
FIG. 12 is a schematic sectional view of the jaw structure of FIG. 11 taken along line 12-12 of FIG. 11 showing the variable resistive matrices in each jaw together with the series and parallel circuits.

Now turning to FIGS. 11 and 12 another embodiment of jaw structure 200 is illustrated that carries cooperating variable resistive matrices as descried above. The upper and lower jaws 212A and 212B have respective engagement surfaces 224A and 224B that carry cooperating variable resistive matrices 125 and 130 as in the previous embodiments of FIGS. 3, 6, 8 and 9. The jaw embodiment of FIGS. 11 and 12 differs in that it is adapted for "one-step" welding and transection of the engaged tissue.

In FIGS. 11 and 12, of jaw structure 200 has an opening-closing mechanism that is capable of applying very high compressive forces on tissue on the basis of cam mechanisms with a reciprocating "I"-beam member 240, wherein jaw closing occurs contemporaneous with Rf energy delivery. Further, the slidable "I"-beam member 240 and the exterior jaw surfaces provide cam surfaces (i) for moving the jaw assembly to the (second) closed position to apply very high compressive forces, and (ii) for moving the jaws toward the (first) open position to apply substantially high opening forces for dissecting tissue. This feature allows the surgeon to insert the tip of the closed jaws into a dissectable tissue plane—and thereafter open the jaws to apply such dissecting forces against tissues. Many prior art instruments are spring-loaded toward the open position and may not be useful for dissecting tissue.

In the embodiment illustrated in FIGS. 11 and 12, the reciprocating "I"-beam member 240 is actuatable from the handle (not shown) of the instrument by any suitable mechanism, such as a lever arm, that is coupled to a proximal end of member 240. The distal end portion 242 of reciprocating "I"-beam member 240 carries first (lower) and second (upper) continuous laterally-extending flange elements 244A and 244B that are coupled by an intermediate transverse element 245. The flange elements 244A and 244B slide in a recessed slot portion 246 in each of the upper and lower jaws (see FIG. 12) to close the jaws and wherein the sliding contact of the lateral edges of flanges 244A and 244B and the side of the recessed slot 246 function to prevent lateral flexing of the jaws. The transverse element 245 and blade edge 250 slide within channels 252 (collectively) in the paired first and second jaws 212A and 212B to thereby open and close the jaws. The transverse element 245 is adapted to transect tissue captured between the jaws with a sharp leading blade edge 250 (FIG. 11). In the embodiment, the "I"-beam 240 also is adapted to provide electrosurgical functionality as it transects tissue and has a polarity that matches that of the jaw bodies 232A and 232B which is slidably contacts. The jaw structure of 200 of FIGS. 11 and 12 is described in more complete detail in co-pending U.S. patent application Ser. No. 10/079, 728 filed Feb. 19, 2002 titled Electrosurgical Systems and Techniques for Sealing Tissue, and U.S. patent application Ser. No. 10/340,144 filed Jan. 10, 2003 titled Jaw Structure for Electrosurgical Instrument and Method of Use, which are incorporated herein by this reference.

Still referring to FIGS. 11 and 12, the first and second jaws 212A and 212B close about an engagement plane 255 wherein the tissue-engaging surface layers 224A and 224B that contact and deliver energy to engaged tissue T as described above. The jaws can have any suitable length with teeth or serrations 256 for gripping tissue (FIG. 11). One preferred embodiment of FIG. 11 provides such teeth 156 at an inner portion of the jaws along channels 248 thus allowing for substantially smooth engagement surface layers 224A and 224B laterally outward of the tissue-gripping elements. The axial length of jaws 212A and 212B indicated at can be any suitable length depending on the anatomic structure targeted for transection and sealing and typically will range from about 10 mm. to 50 mm. The jaw assembly can apply very high compression over much longer lengths, for example up to about 200 mm., for resecting and sealing organs such as a lung or liver. The scope of the invention also covers jaw assemblies for an instrument used in micro-surgeries wherein the jaw length can be about 5.0 mm or less.

Figure 13:
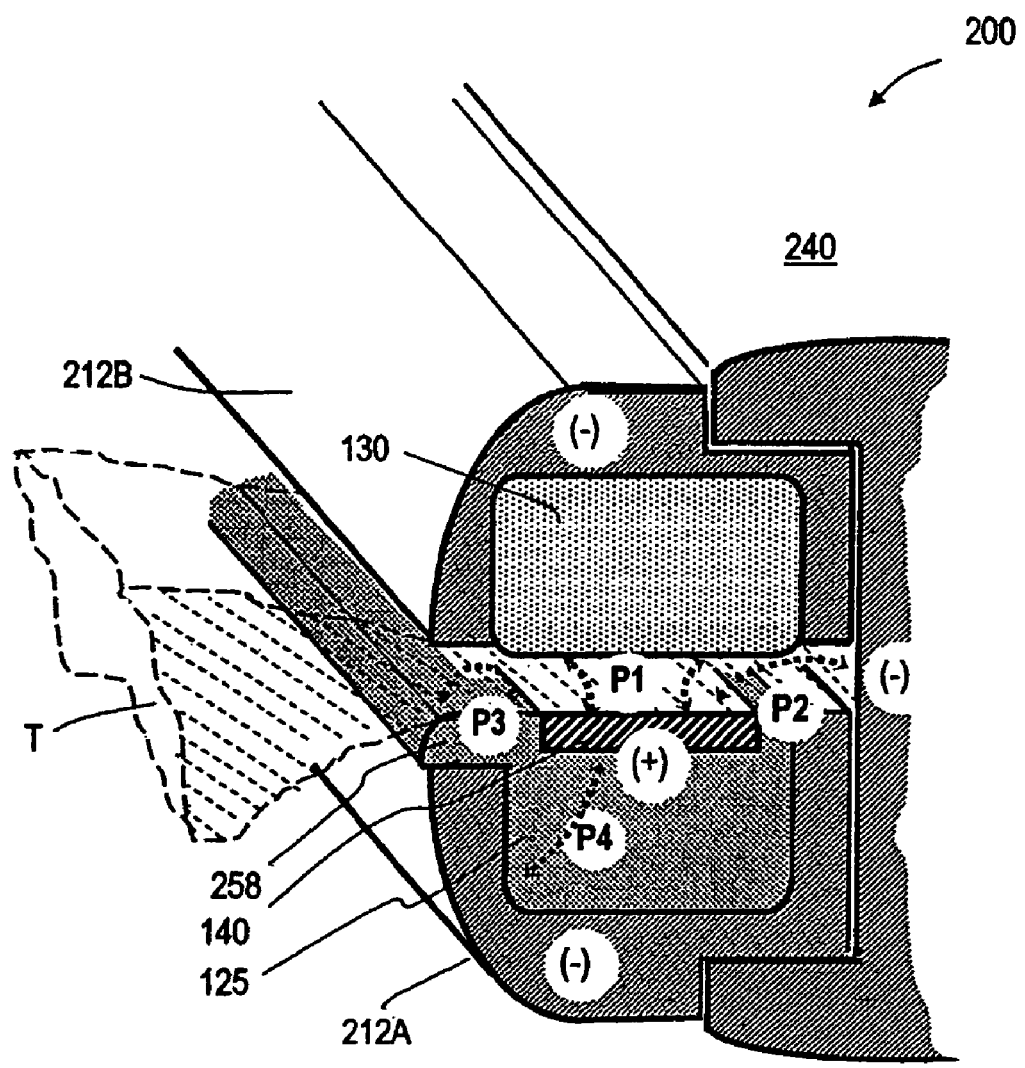
FIG. 13 is an enlarged sectional view of a portion the jaw structure of FIGS. 11-12 showing the potential current paths in engaged tissue and the variable resistive 3D matrix bodies during operation.

In FIGS. 11 and 12, it can be seen that the lower jaw 212A has a variable resistive matrix 125 that has an edge portion 258 that (optionally) extends laterally over the outer edge of the jaw body 232A. This matrix feature has been found useful in modulating Rf energy density in the margin of the treated tissue to create distinct region between welded tissue and unaffected tissue. Also, the upper jaw's matrix 130 is positioned to extend slightly outward (dimension 262) from the upper jaw body 232B. FIG. 13 illustrates that the jaw structure 200 of FIGS. 11 and 12 provides the multiplicity of flow paths P1-P4 as described previously in FIGS. 10A-10D. In all other electrosurgical aspects, the jaw structure 200 and variable resistive matrices of FIGS. 11 and 12 functions as described above with reference to FIGS. 3, 6, 8, 9 and 10A-10D.

Figure 14A:
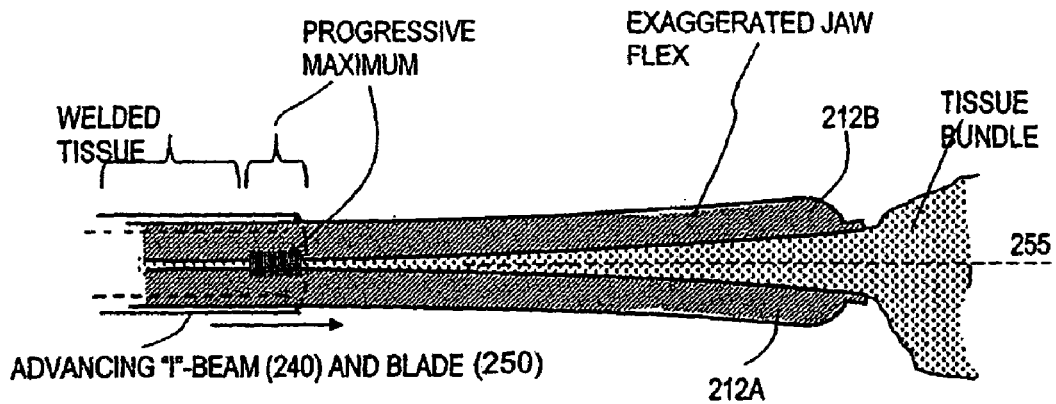
FIGS. 14A-14C are schematic sectional views of the jaw structure of FIGS. 11-13 with elongate jaws progressively engaging, welding and transecting a tissue bundle.
Figure 14B:
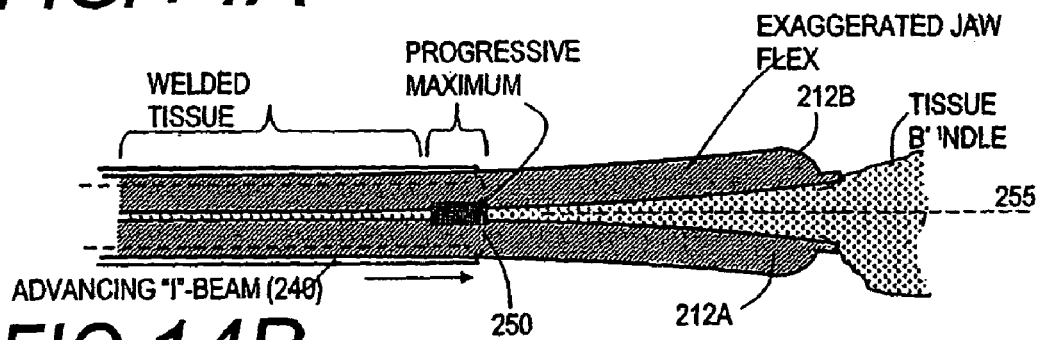
Figure 14C:
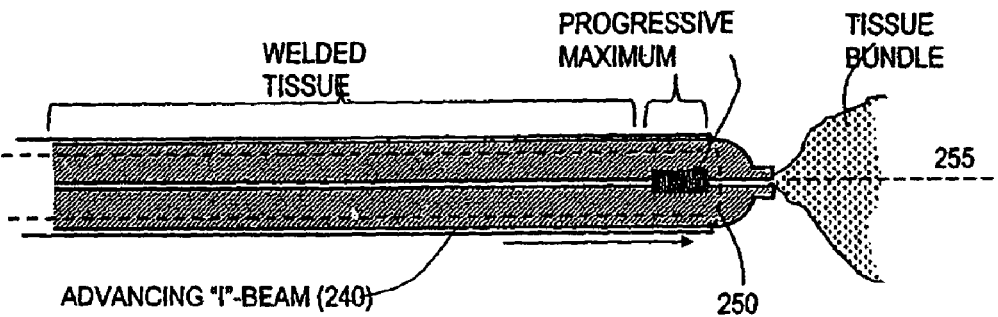

Of particular interest, FIGS. 14A-14C graphically illustrate the one-step sealing and transection method of the invention. When using elongated jaws in a small diameter instrument, the issue of jaw flexure when clamping thick tissue bundles typically creates difficulties for both sealing and transection. The jaw structure 200 of FIGS. 11 and 12 solve such problems by applying Rf energy contemporaneously with jaw closure. Initial Rf energy delivery will begin to dehydrate the engaged tissue T thus making it possible to compress the tissue to a thin membrane. At the same time, the matrices 125 and 130 will modulate Rf ohmic heating axially along the length of the jaws to thereby insure that thin treated tissue regions in the proximal jaw are not being ohmically heated while more distal regions of the engaged tissue are receiving maximal ohmic heating. All the while, each tissue region containing a different tissue type will receive the optimal Rf energy density based on impedance matching with the adjacent region of a variable resistive matrix.

In FIGS. 14A-14C, the jaws 212A and 212B are shown with greatly exaggerated flex characteristics to illustrate, in effect, a method of the invention. The "I"-beam 240 can compress the tissue T dramatically as it is progressively welded. Thus a very small jaw structure 200 in a 5 mm. diameter device can chomp down on, weld and transect very thick tissue bundles that are initially up to ½ inch or even 1 inch thick. The highest ohmic heating progresses in a "front" across the tissue and is automatically modulated by the variable resistive matrices 125 and 130 and series-parallel circuitry as described above. The jaw structure 200 further allows the surgeon tactile feedback of the tissue welding process as the advancement of the "I"-beam" 240 indicates that the tissue is welded. This inventive method for welding tissue can be most accurately summarized as the microscale modulation of ohmic active heating in engaged tissue as depicted in FIGS. 10A-10D combined with the progressive macroscale application of ohmic heating as in FIGS. 14A-14C as the blade 245 transects the engaged tissue. The one-step welding and transecting functionality is provided by the high compression "I"-beam for jaw closure and tissue transection together with the cooperating variable resistive components 125 and 130 of the jaw structure.

Figure 15:
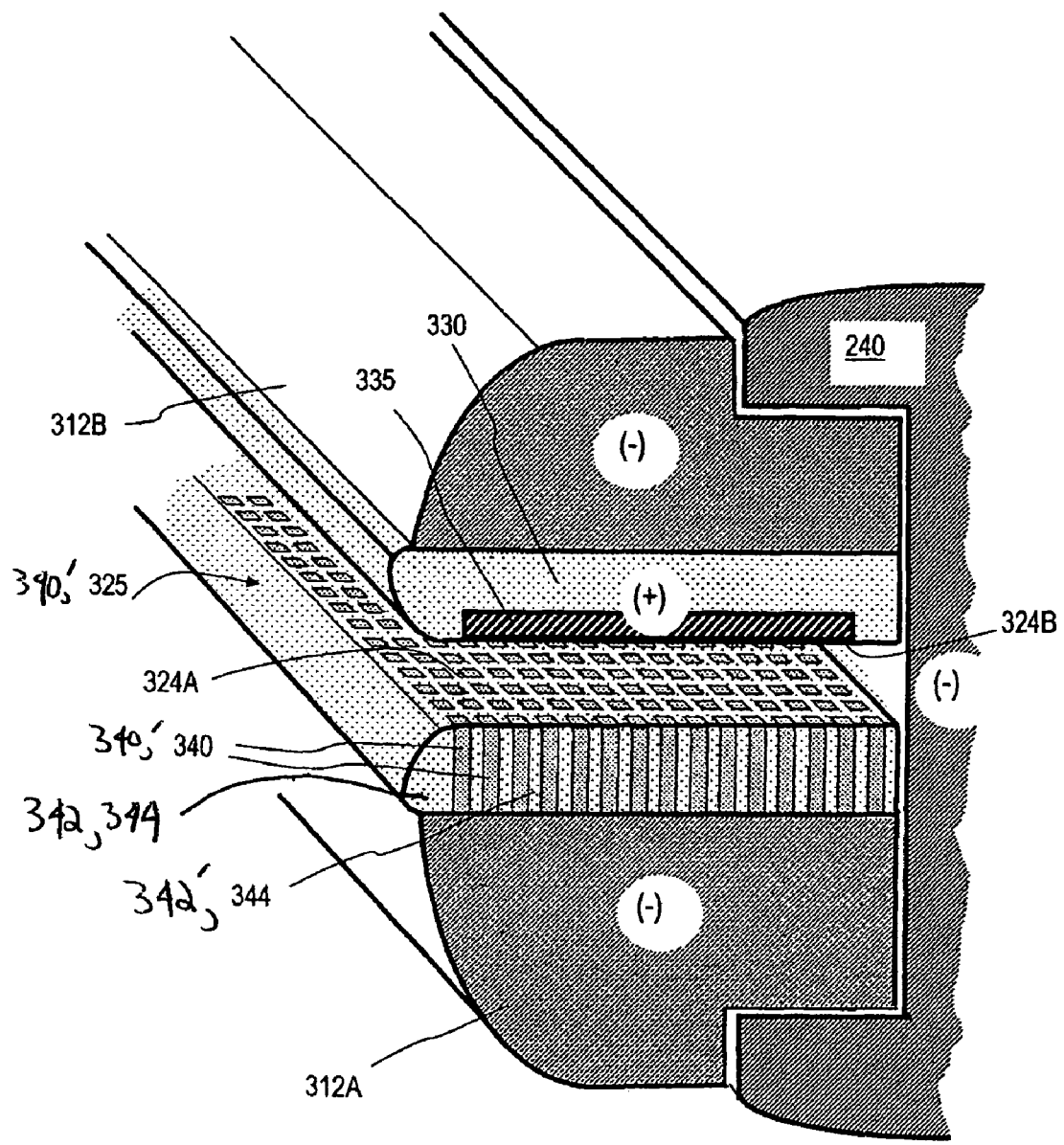
FIG. 15 is a perspective view of a portion of an alternative jaw structure similar to that of FIGS. 11-13 with a variable resistive matrix having a pixelated configuration.

3. Pixelated variable resistive engagement surfaces. FIG. 15 illustrates a portion of an alternative working end 310 corresponding to the invention with first and second jaws 312A and 312B and respective tissue-engaging surfaces 324A and 324B in a jaw-closed position. The working end 310, in general, is similar to that illustrated in FIGS. 11-13. In the embodiment of FIG. 15, the engagement surfaces again include variable resistive matrices of a polymeric material the exhibits a positive temperature coefficient of resistance (PTC or PTCR) effect. The lower jaw 312A carries a microfabricated matrix 325 that is best described as a pixelated PTCR matrix. The upper jaw carries a matrix 330 that is similar to that described in previous embodiments together with an exposed electrode 335 in a central portion of the engagement surface 324B. The jaw structure of FIG. 15 reverses the location of exposed electrode 335 from that illustrated in FIGS. 9, 11 and 12, with no change in functionality. Of particular interest, the matrix 325 of lower jaw 312A defines a plurality of polymeric composite PTCR pixels 340 (collectively) spaced apart in a field 342 comprising a field material 344. In various embodiments, pixels 340 can comprise a pixel array 340'. Each pixel 344 of array 340' can be configured to be independently switchable depending upon the temperature of engaged tissue adjacent the pixel as is described herein.

Field 342 is also described as a non-pixel field comprising a plurality of non-pixel portions 342'. In various embodiments, field material 344 can comprise a substantially electrically insulative material such as a electrically insulative polymer or a ceramic, an electrically and thermally insulative material, a materially having a substantially fixed electrical resistance, or a material having a negative temperature coefficient of resistance (NTC or NTCR). In many embodiments, field material 344 can comprise an electrically insulative polymer which in one embodiment can be the same polymer as pixels 340, but with substantially no conductive filler. In FIGS. 15-23, the PTCR pixels 340 are shown as having rectangular or polygonal shape at the engagement surface 324A. It should be appreciated however, that the pixels 340 can have any number of surface shapes or contours, for example convex, concave, curvilinear, etc. Also pixels 340 can have any highly elongated linear or curvilinear form at engagement surface 324A.

Figure 16:
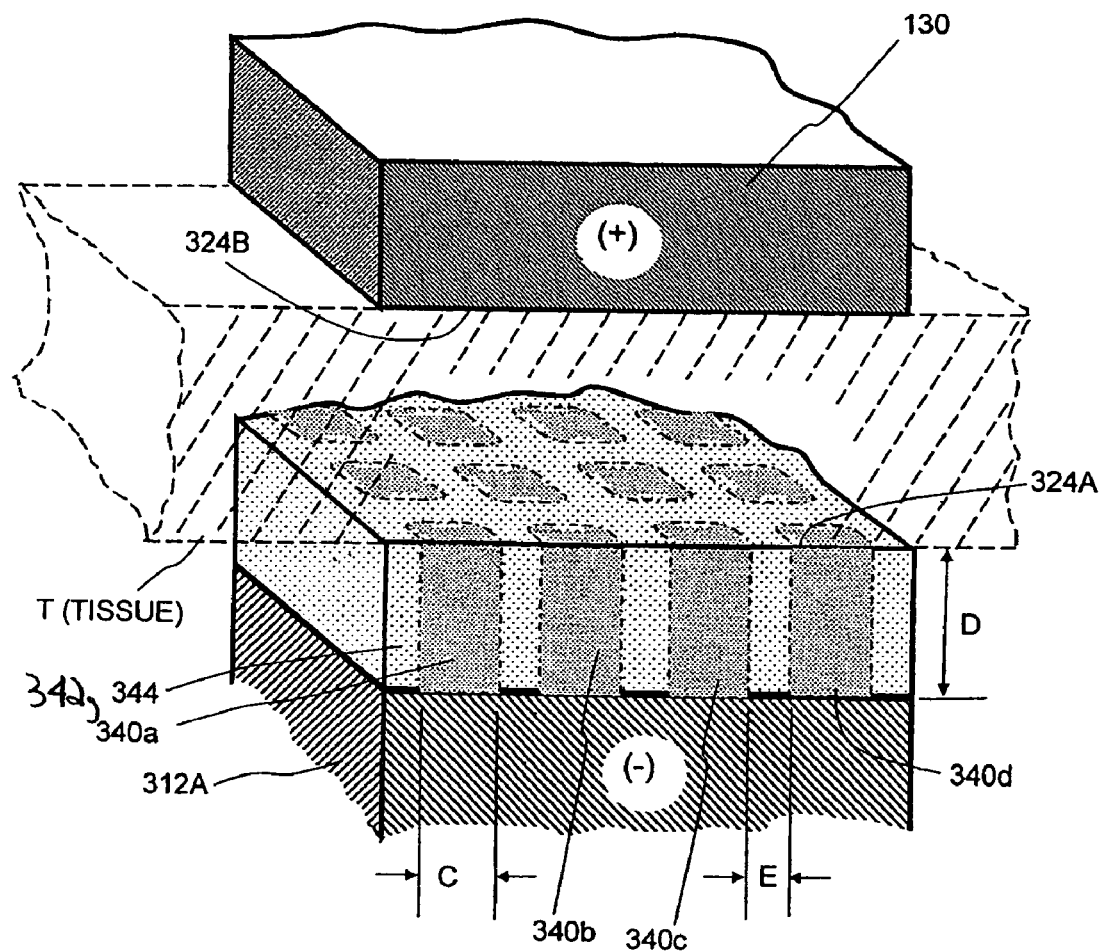
FIG. 16 is an enlarged cut-away view of several pixels of the variable resistive matrix of FIG. 15.

Referring to FIGS. 15 and 16, in a preferred embodiment, field material 344 is an electrically non-conductive polymer (e.g., a polyethylene, silicone, etc.) that has one or more material properties similar to that of the PTCR pixels 340. Such similar properties can include without limitation, Young's modulus, durometer (e.g., Shore A or Shore D rating) and the like. For convenience, pixels 340 are shown as substantially square pixels in FIGS. 15 and 16. However, it should be appreciated that in various embodiments, PTCR pixels 340 can have any number of round, oval, rectangular or polygonal cross-sectional shapes including combinations thereof. Also the shapes of pixels 340 can be homogeneous or heterogeneous including two or more different shapes. The shape of pixels 340 can be configured to achieve selectable thermal, electrical and mechanical properties or a combination of properties (e.g., thermal or electoral conductivity, etc.) for matrix 325 and/or engagement surfaces 224A and 224B. For example, smaller sized pixels can be employed to obtain a high resolution, finer or otherwise more precise spatial control of current paths and/or to have faster thermal response times (e.g. faster switching times or time constants) due to faster thermal conduction in smaller pixel areas. In related embodiments, one portion of matrix 325 can be configured with a first pixel size or combination of pixel sizes to have a first time constant and a second portion can be configured with a second pixel size or combination of sizes to have a second time constant. In various embodiments the selected pixel size, can be an average pixel size with a selected standard deviation. Also, the combination of pixel sizes can be a range of pixel sizes, and can also include a bimodal or other multi-model distribution of pixel sizes.

In particular embodiments, matrix 325 can include portions having different shaped pixels, for example a first portion having a first shaped pixel and a second portion having a second pixel shape. Alternatively the matrix 325 can include combination of homogenous and heterogeneous pixel shape portion. For example, in one embodiment, the matrix can include one or more heterogeneous portions and a one or more homogenous portions. The placement and combination of such portions can be configured to produce selectable thermal, electrical and/or mechanical properties.

Referring now FIG. 16, the individual PTCR pixels are indicated at 340a-340d. The dimension C across a minor axis of a pixel 340 can range from about 1 micron to 1000 microns, and more preferably from about 50 to 500 microns. The thickness dimension D of the matrix 325 that corresponds to the height of pixels 340 can range from about 100 microns to 3 mm. The spacing E between the pixels 340 can range from about 5 to 1000 microns. As can be seen in FIG. 16, the pixels 340 extend from the engagement surface 324A through the full thickness of matrix 325 to contact the jaw body 312A which functions as an electrode as it is coupled to electrosurgical energy source 150A. In various embodiments, the matrix can have a durometer in the range from about 20 to 95 Shore A range, or in the range from about 45-80 Shore D range. These Shore A and Shore D hardness ratings encompass material properties (e.g. durometer, elasticity, etc.) that have been found useful in particular embodiments. However, they are exemplary and in other embodiments, different ranges can be used, e.g. greater than 95 Shore A or greater than 80 Shore D. They can also be converted to equivalent Young's modulus, IRHD values (International Rubber Hardness Degree) and the like.

Figure 17A:
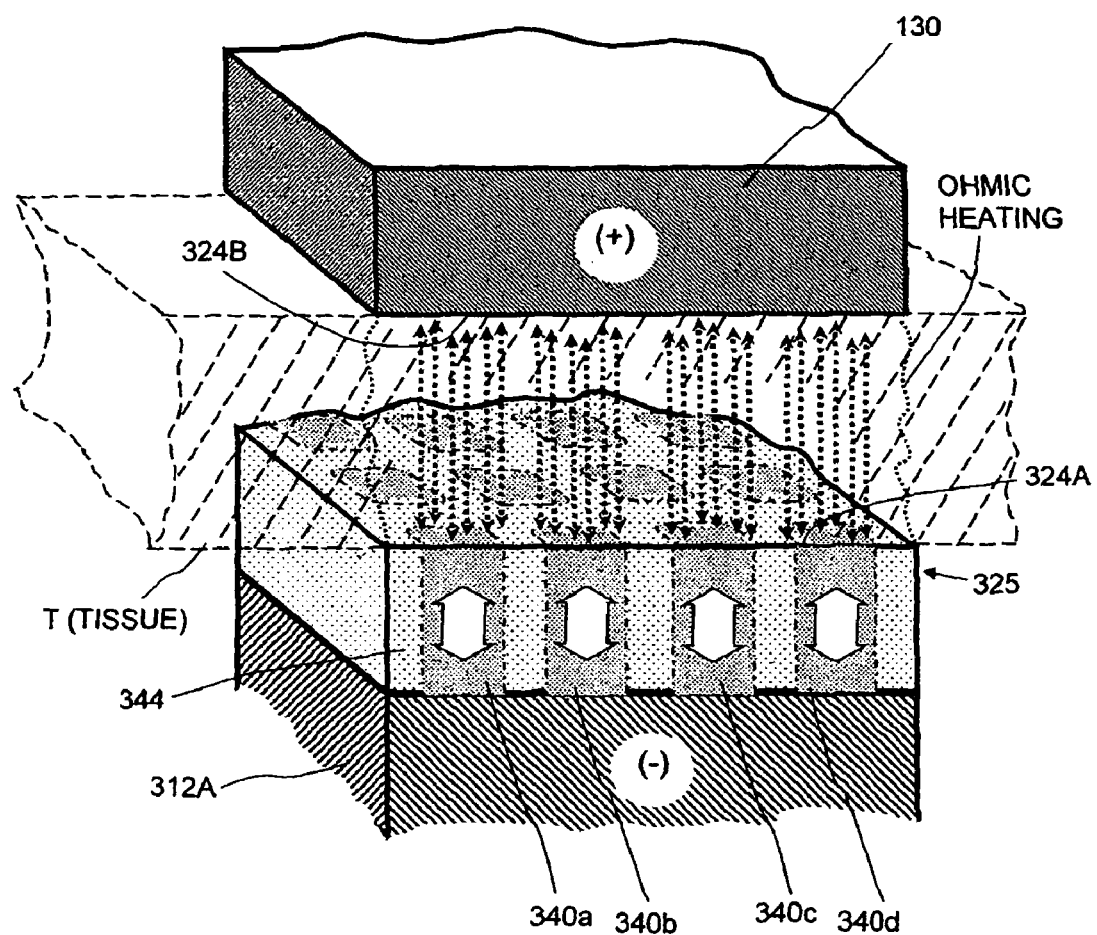
FIG. 17A is a cut-away view similar to FIG. 16 illustrating a first step in a method of using the pixelated variable resistive matrix of FIG. 16.
Figure 17B:
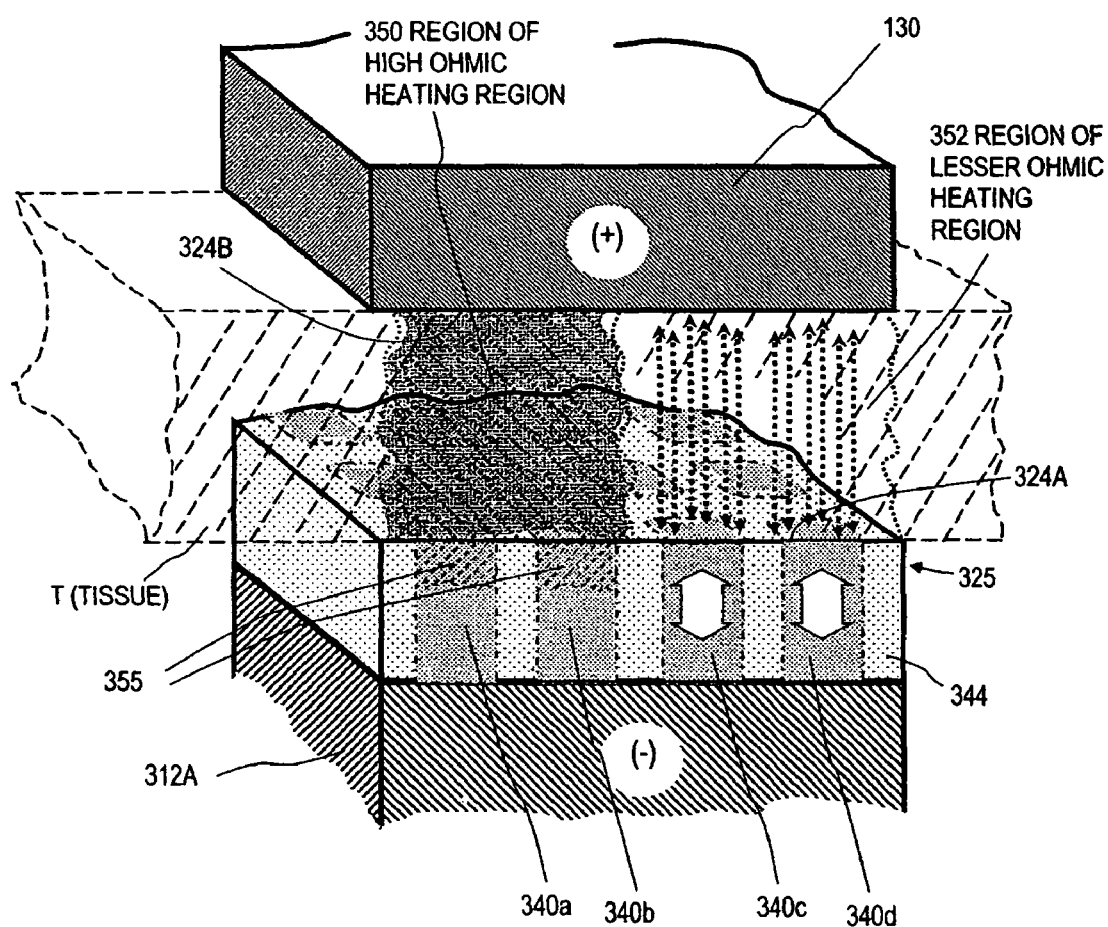
FIG. 17B is another cut-away view illustrating a second step in a method of using the pixelated variable resistive matrix of FIG. 16.

FIGS. 17A-17B illustrate the method of using the pixelated matrix 325 in at least one jaw of an electrosurgical instrument. The PTCR pixels 340 function as temperature responsive components as described above, but with the (i) temperature sensing functionality and (ii) the Rf energy delivery functionality being distributed to a plurality of discrete regions, or pixels, over the engagement surface 324A. FIG. 17A depicts the step of energizing the working end wherein Rf current flows are indicated at P in tissue T as the current flows between the opposing polarity electrodes 312A and 335 via the PTCR pixels 340a-340d. The block arrows in each pixel 340a-340d indicate current flow therethrough which is allowed at any time the pixel is below its switching range. In FIG. 17A, it can be understood that electrical current cannot flow through the field portion 342 (Note change 344 in drawing to 342) of matrix 325 since it is a non-conductive polymer. It is known that Rf current tends to jump off "edges" of a conductor when interfacing with a less conductive media, such as tissue. Thus in various embodiments, the plurality of PTCR pixels 340 can be configured as a myriad of such "edges" to induce current to propagate from the engagement surface. In this way, PTCR pixels 340 can be utilized to control the induction and flow of current from the engagement surface to tissue. In FIG. 17A, it can be easily understood that alternating Rf current will then cause ohmic heating in the engaged tissue T, which is along the idealized current paths P in the tissue. The resolution of the PTCR pixels 340 can be specified to be sufficiently fine so that ohmic heating occurs in a substantially continuous and uniform manner across the dimension of the engagement surfaces 324A and 324B. In FIG. 17A, the idealized current flow paths P indicate that the PTCR pixels 340 are below the switching range (the PTCR effect) of the polymeric composition thus causing Rf energy density, and resultant ohmic heating, in the engaged tissue T.

Now turning to FIG. 17B, it can be seen that the next step of the method relates to the use of the pixelated matrix 325 in its temperature responsive role to adjust its resistivity in response to adjacent tissue temperature. In FIG. 17B, the region 350 of tissue T adjacent to pixels 340a and 340b is indicated by cross-hatching as being ohmically heated above the switching range of the PTCR pixels. The other tissue region 352 adjacent to pixels 340c and 340d still carries current flow in paths P and ohmic heating continues—but thermal effects remain below the switching range of the adjacent PTCR pixels 340c and 340d. Such differential thermal effects in tissue caused by ohmic heating are the norm, as tissues differ greatly in hydration before Rf application, and dynamically change during the course of Rf application. The desiccation of tissue plays a major role in ohmic heating, and well as tissue type (i.e., collagenous tissue, fatty tissue, etc.). As can be seen in FIG. 17B, the highly ohmically heated tissue region 350 conducts heat back to the surface regions 355 of the pixels 340a and 340b thereby elevating these pixel surfaces 355 to above the switching range of the material. By this means, PTCR pixels 340a and 340b terminate current flow to the tissue. In other words, the pixels function as discrete "on-off switches" to either allow or disallow current flow therethrough to the immediately adjacent tissue. The working surface 324A thus can be considered to provide micron-scale localized on-off control of Rf application to engaged tissue based on micron-scale local temperature sensing. These and related embodiments provide a means for controlling Rf application to tissue with highly spatially distributed temperature sensing and response—exactly at the engagement surface 324A. In, use, this approach allows for a more rapid and spatially precise control of energy application resulting in more uniform thermal effects in the target tissue including more uniform heating and welding with a reduced incidence of desiccation and charring. Further, embodiments of this method of thermal tissue treatment using pixilated PTCR materials to control energy application can be accomplished without thermocouples or feedback circuitry This approach differs markedly from other thermal sensing systems that may use a single sensor coupled to feedback circuitry and controller algorithms.

Of particular interest, referring to FIG. 17B, it can be understood that each pixel 340a-340b will respond and change temperature at and about the engagement surface 324A. The actual "switched" region of each pixel 340a-340b thus is indicated at 355, wherein the temperature exceeds the PTCR material's switching range. In preferred embodiments, the field material 344 is substantially thermally insulative so as to enhance the effect of causing the switched regions 355 of the pixels 340 (collectively) to remain as close as possible to the engagement surface 324A. By inducing the actual "switching" region 355 of the pixels 340 to remain proximate the engagement surface, it has been found that the speed of switching the pixels off and on can be increased—that is, switching the pixels 340 between high (current-limiting) resistance and low (current-permitting) resistance. This speed-of-switching effect depends on thermal relaxation of the tissue, and thereafter the speed at which the pixels 340 can thermally relax in response to the tissue's thermal relaxation. For these reasons, the insulative field material 344 preferably has a thermal conductivity of less than about 10 W/m-K which insures that it is not retaining heat to conduct back to the pixels. Preferably, the field material 344 has a thermal conductivity of less than about 5 W/m-K, and more preferably less than about 2 W/m-K. These properties can be provided in known polyethylene and silicone polymers, and well as other polymers described above.

In various embodiments, the pixelated matrix 325 of FIGS. 15-17B, or other embodiments described herein can be microfabricated using suitable polymers by several different techniques collectively known as soft lithography. For example, in one embodiment for fabricating the matrix, microtransfer molding can be used wherein a transparent, elastomeric polydimethylsiloxane (PDMS) stamp has patterned relief on its surface to generate features in the polymer. The PDMS stamp is filled with a prepolymer or ceramic precursor and placed on a substrate. The material is cured and the stamp is removed. The technique generates features as small as 250 nm and is able to generate multilayer systems that can be used to fabricate the pixels and polymeric field in which the pixels reside. Replica molding is a similar process wherein a PDMS stamp is cast against a conventionally patterned master. A polyurethane or other polymer is then molded against the secondary PDMS master. In this way, multiple copies can be made without damaging the original master. The technique can replicate features as small as about 50 to 100 nm. Another process is known as micromolding in capillaries (MIMIC) wherein continuous channels are formed when a PDMS stamp is brought into conformal contact with a solid substrate. Then, capillary action fills the channels with a polymer precursor. The polymer is cured and the stamp is removed. MIMIC can generate features down to 1 µm in size. Solvent-assisted microcontact molding (SAMIM) is also known wherein a small amount of solvent is spread on a patterned PDMS stamp and the stamp is placed on a polymer, such as photoresist. The solvent swells the polymer and causes it to expand to fill the surface relief of the stamp. Features as small as 100 nm have been produced. A background on soft lithography microfabrication is found in Xia and Whitesides, Annu. Rev. Mater. Sci. 1998 28:153-84. In another embodiment for fabricating the pixelated matrix 325, the polymer material comprising the matrix can be extruded using extrusion methods known in the art to disperse or otherwise provide the PTCR pixels 340 within a polymeric field material 344. The extruded material then can be cut into selectable slices to make individual thin pixilated PTCR matrices. The extruded material can be also processed using a variety of polymer processing methods known in the art, e.g., calendaring, etc, to produce selectable matrix thickness or other matrix dimension. In one embodiment the pixel material can be co-extruded with field material.

Figure 18:
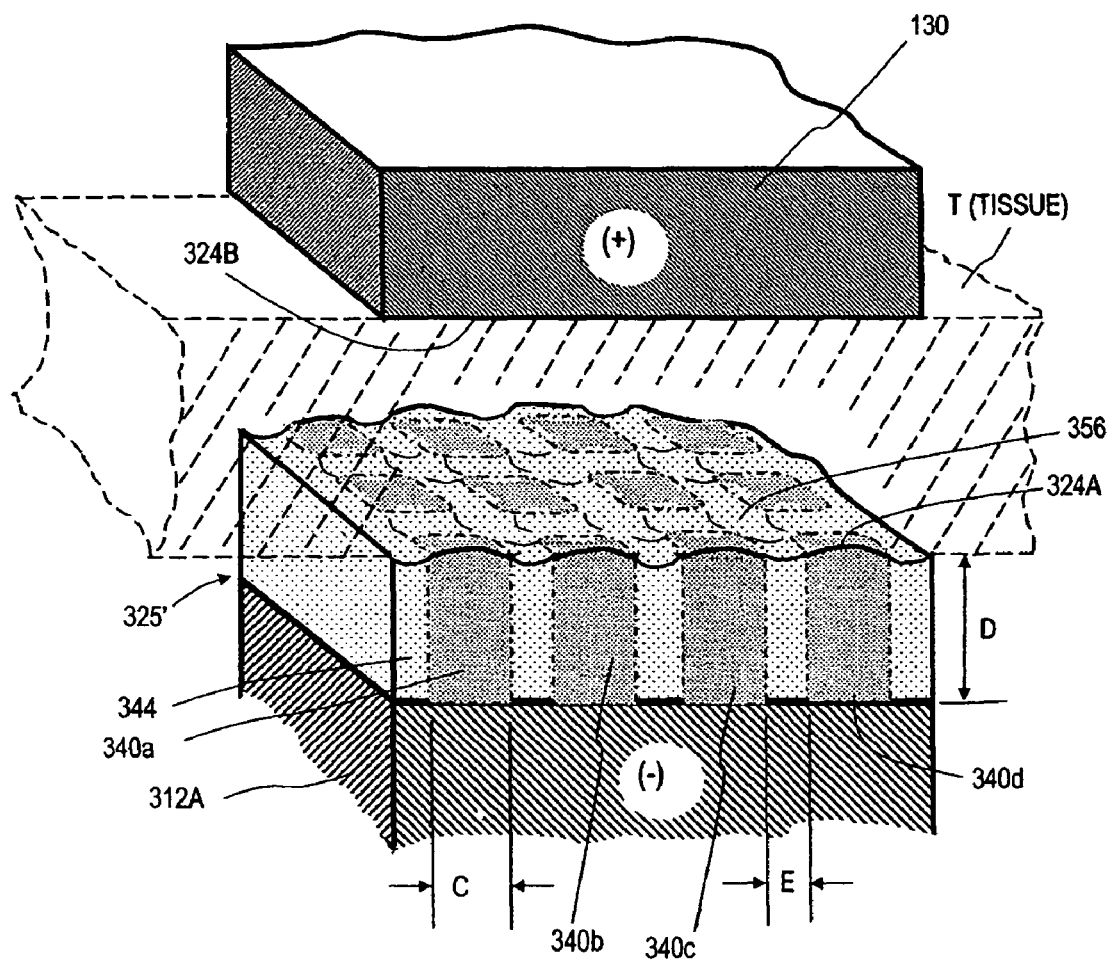
FIG. 18 is a cut-away view of an alternative variable resistive matrix with PTCR polymeric pixels and polymeric field materials having different durometers for providing dynamic surface relief.

FIG. 18 illustrates an alternative embodiment of matrix 325' wherein pixels 340 and the field material 344 having differing durometer and/or elastic moduli. As shown in FIG. 18, the jaw engagement surfaces 324A and 324B are in a closed position with the engaged tissue T under very high compression developed by the translating beam 240 as can be understood from FIGS. 12, 13 and 15. In the lower engagement surface 324A of FIG. 18, it can be seen that the lower modulus composition 344 is more compressible about the interface with the tissue T. This aspect of the invention has been found useful for multiple purposes. First, the spatially variable moduli in the engagement surface 324A provides a dynamic form of tissue-gripping structure for grippably engaging the tissue T during modulated Rf application. In other words, the engagement surfaces provides a dynamic, projecting grip structure that provides for greater surface relief under high tissue compression, just when greater gripping is required. As described above, the instrument of FIGS. 12, 13 and 15 can weld and transect tissue in "one-step", and it is desirable to have a surface gripping structure that insures that the tissue does not slip laterally as it is being welded and transected. Further, it is believed that local recesses 356 of the low modulus polymer 344 in the engagement surface 324A are beneficial during the tissue-welding process. As the tissue-welding process occurs, fluid that initially migrates from the tissue can be captured in the recessed regions 356 of the engagement surface and hydrate the tissue as it increases in temperature—rather than escaping laterally from the jaw structure. In an alternative embodiment, the Young's modulus and/or durometer of the pixels 340 and the insulative field material 344 can be reversed. In other words, the pixels 340 can be configured to have a lower modulus and be more compressible than the field material 344, which again will dynamically grip tissue and localize moisture in the transiently recessed portions.

Figure 19:
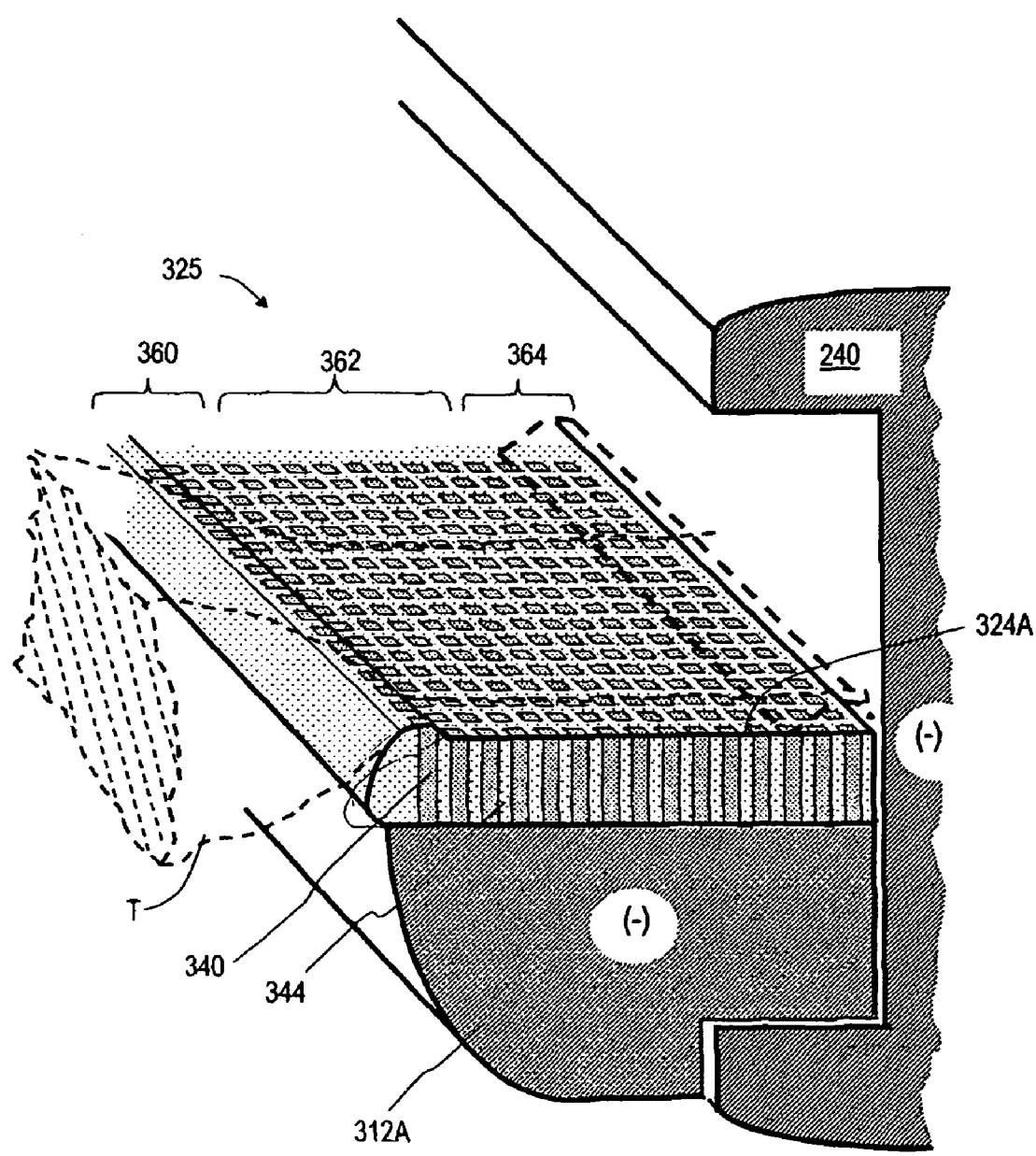
FIG. 19 is a perspective view of an alternative jaw engagement surface with edge regions having a higher durometer or modulus than non-edge regions.
Figure 20:
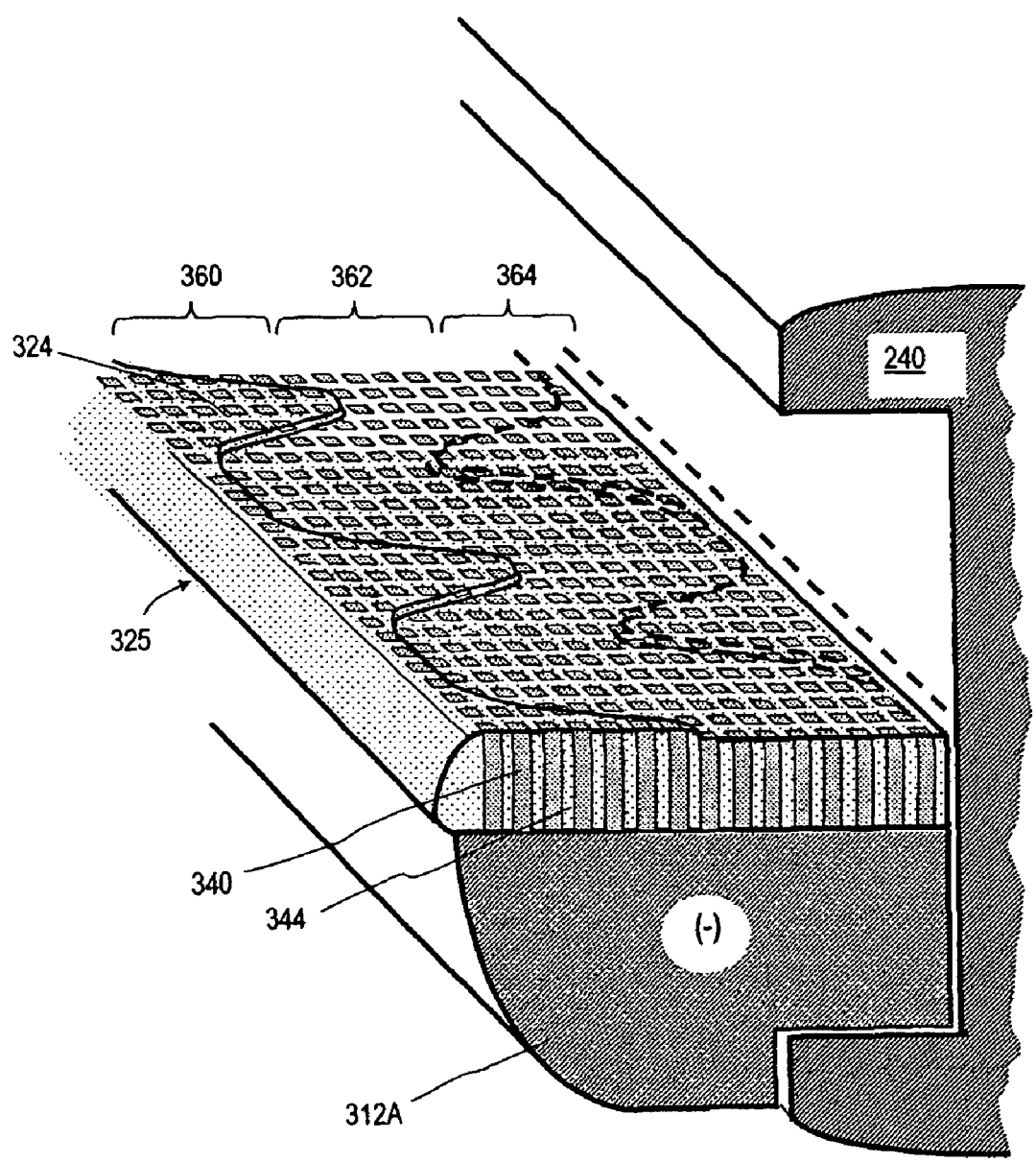
FIG. 20 is a view of an alternative jaw engagement surface with an elevated edge region of a higher durometer or modulus.

In order to grip tissue, the alternative embodiment of FIG. 19 further provides at least one edge region 360 of resilient engagement surface 324A (e.g., pixels 340 and field material 344) in a material having a higher Young's modulus (or durometer) than the central region 362 of the surface. In FIG. 19, the upper jaw is not shown for clarity of illustration. FIG. 19 depicts the higher modulus outer edge region 360 engaging tissue (phantom view) about the jaw periphery while the central lower modulus region 362 of engagement surface 324A is compressed under the strength of the jaw closing mechanism. It should be appreciated that the second or inner side 364 of the engagement surface 324A of FIG. 19 also can have a higher modulus edge region (phantom view). FIG. 20 illustrates an alternative design of engagement surface 324A wherein first edge region 360 in its repose state is more elevated than the central region 362 of the engagement surface. Further, the first edge region 360 can have a zigzag or other similar angular form for enhanced gripping of tissue. In FIG. 20, the inner edge 364 of engagement surface 324A (phantom view) also can be "elevated" (greater surface relief) in its repose state or can have a higher modulus than the central lower modulus region 362.

Figure 21:
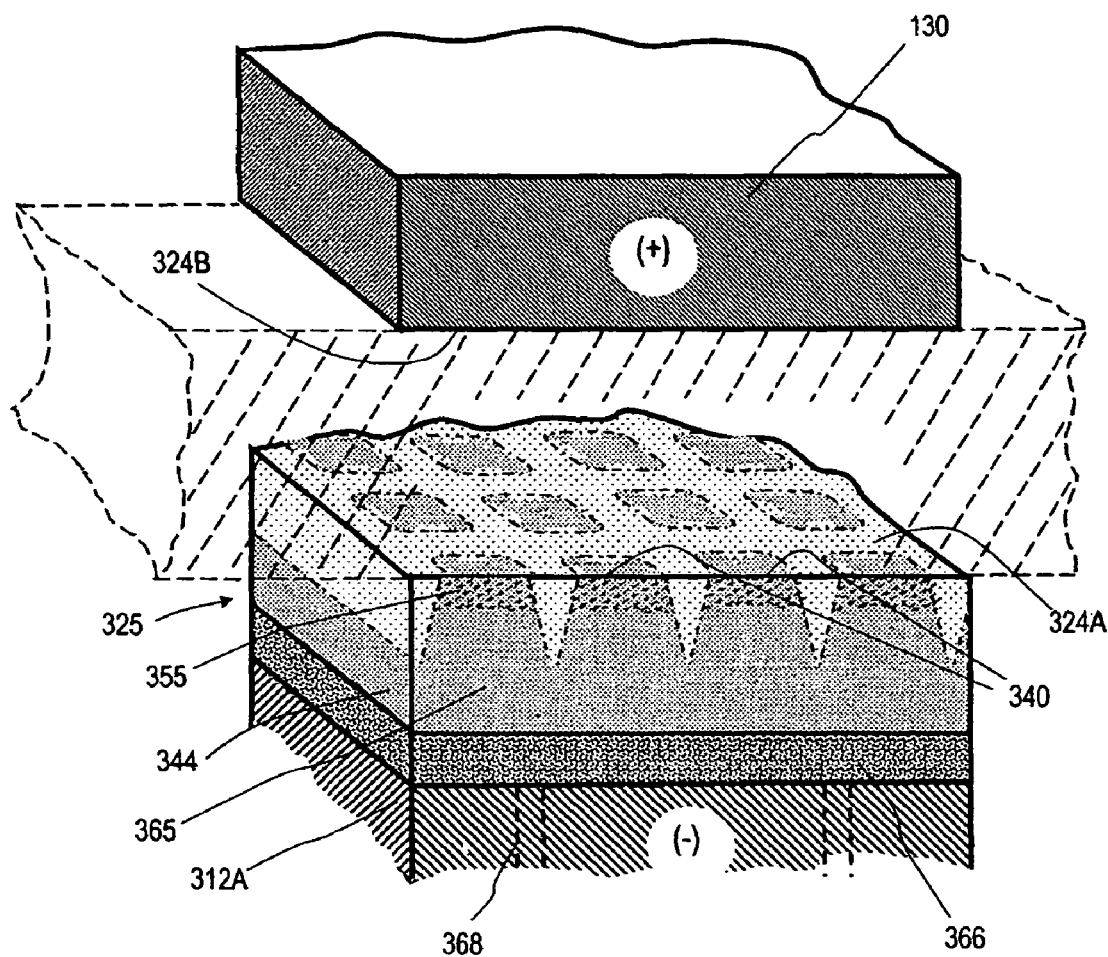
FIG. 21 is a view of an alternative pixelated matrix similar to that of FIG. 16.
Figure 22:
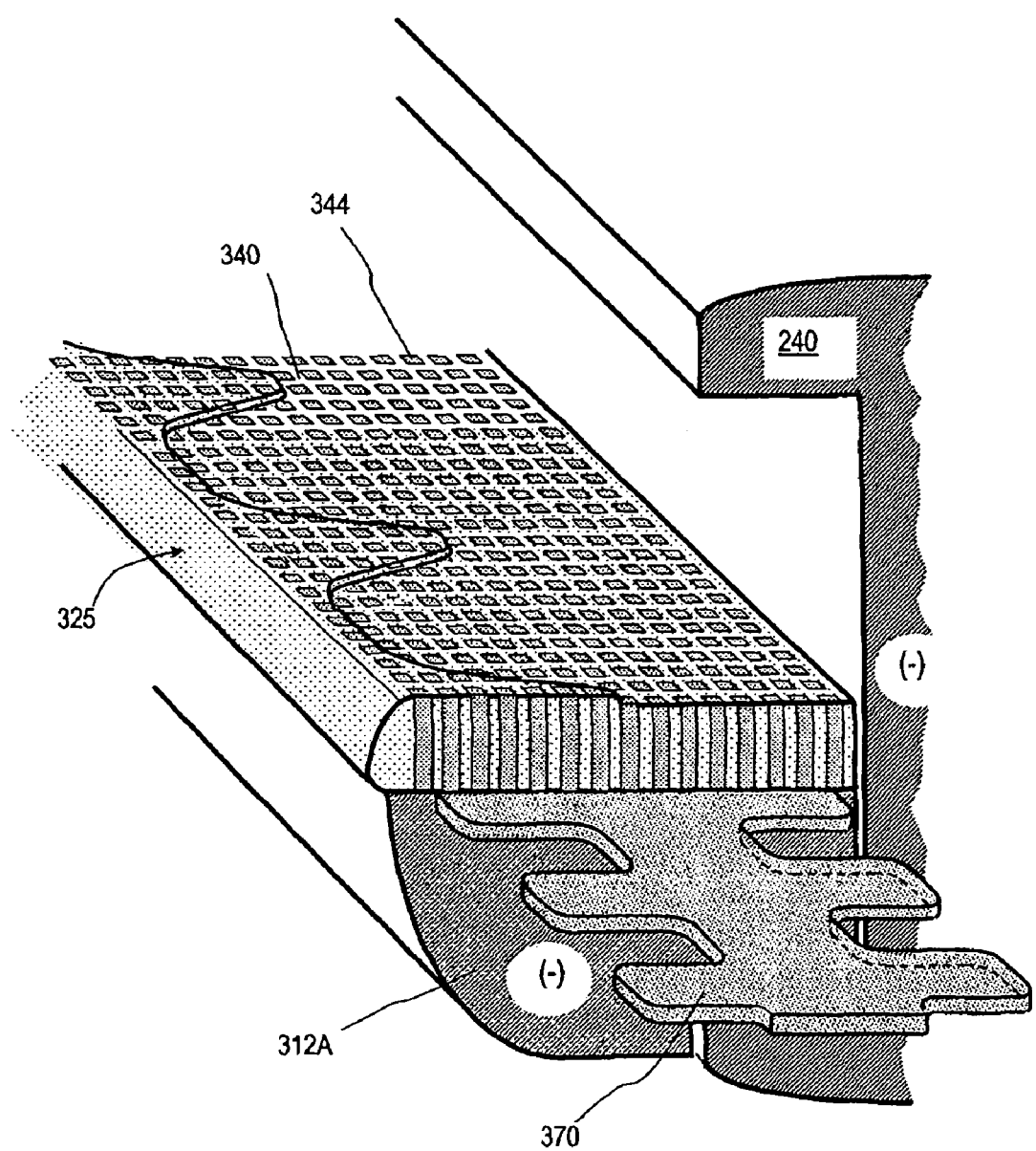
FIG. 22 is a perspective view of an alternative jaw engagement surface with a resilient polymer component at an interior of the jaw.

FIG. 21 is another embodiment of matrix 325 wherein the pixels 340 and polymeric field 344 are configured and molded in an alternative manner. As can be seen in FIG. 21, the engagement surface 324A again exposes the pixelated regions of a PTCR composition for sensing tissue temperature and on-off switching of Rf current flow in a pixel-by-pixel manner. In FIG. 21, the cross-sectional view of the matrix 325 illustrates that the PTCR pixels 340 can have a tapered form and extend from a continuous base portion 365 of the PTCR polymer. The insulative polymer field material 344 is then molded around the pixels 340 to provide the insulated region of the engagement surface about the spaced apart exposed pixels. As can be seen in FIG. 21, the surface regions 355 of each pixel 340 then would form the active current-switching region of the PTCR composition, which is comparable to FIG. 17B. The matrix 325 of FIG. 21 also illustrates another optional component of the electrosurgical working end that comprises a resilient body 366 that comprises a compressible cushion underlying the matrix 325. The resilient body 366 can be any rubber-like material that allows its compression so as to accommodate thicker tissue volumes engaged by the jaws 312A and 312B (see FIG. 15). The resilient body 366 also can be an open cell type of material in which case at least one vent 368 can be provided in the jaw to better allow compression and decompression of the body 366. In one embodiment, the resilient body 366 can be a conductively doped polymer, in order for the matrix 325 to conductively coupled with the jaw body 312A. Alternatively, any other conductive clip can be provided to couple the interior of matrix 325 to the jaw body 312A. FIG. 22 illustrates a working end that has an alternative resilient body 370 that can underlie the matrix 325. In this case, the resilient body 370 has a cut-out shape to provide space for compression of the resilient material to better allow overall compression of matrix 325 in at least one jaw when engaging thick tissue volumes.

Figure 23:
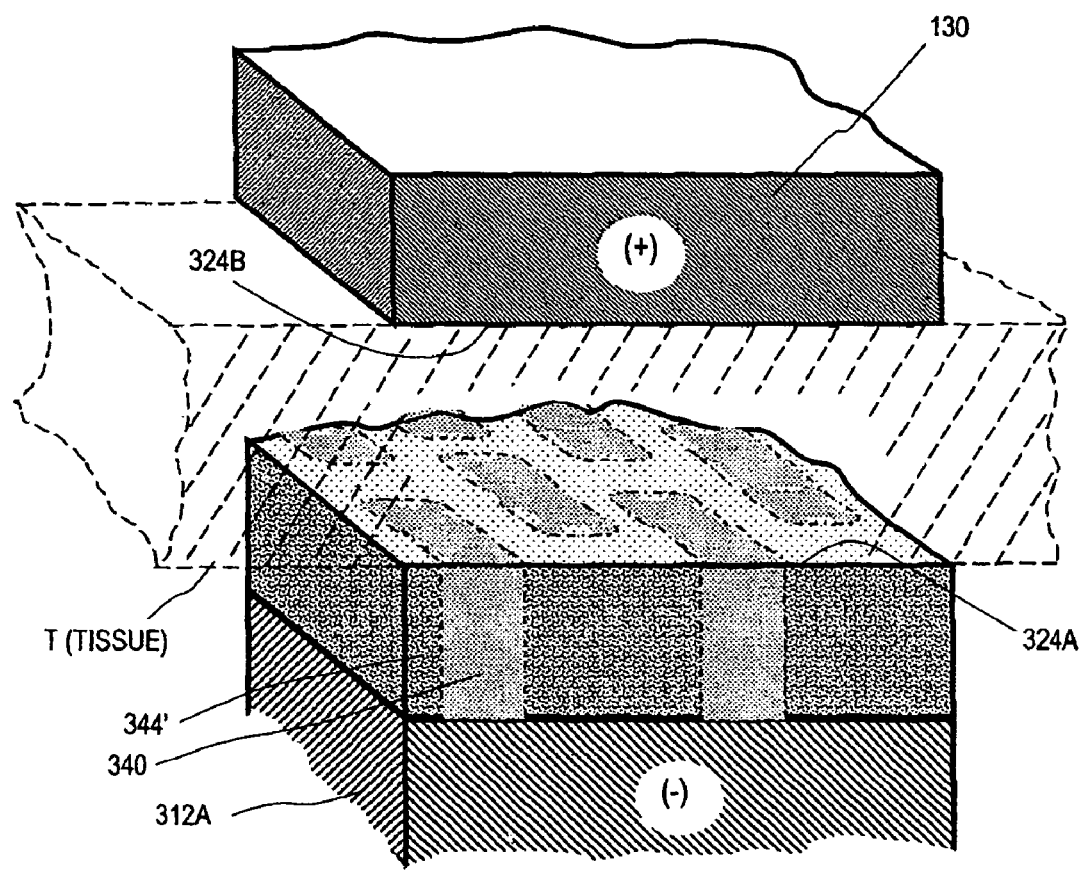
FIG. 23 is a view of an alternative pixelated matrix wherein the polymeric pixel composition and the field composition are of different PTCR materials.

In another embodiment illustrated in FIG. 23, the pixelated engagement surface 324A can be formed of first and second differing polymeric PTCR compositions. In other words, the field PTCR composition 344' can have a low switching range wherein it responds to a low temperature in the ohmically heated adjacent tissue to thereby switch off Rf current, for example in the 80° to the 120° C. range. The PTCR composition of the pixels indicated at 340' has a higher switching range wherein it responds only to a higher temperature in the adjacent ohmically heated tissue to thereby switch off current, for example in the 120° to the 300° C. range. The use of two differently performing PTCR composites in an engagement surface 324A has the advantage of rapidly elevating the ohmic heating in the engaged tissue T until the lower-switching matrix turns off, and thereafter functioning as described above with the higher-switching pixels 340' providing controlled Rf application to the engaged tissue.

Figure 24:
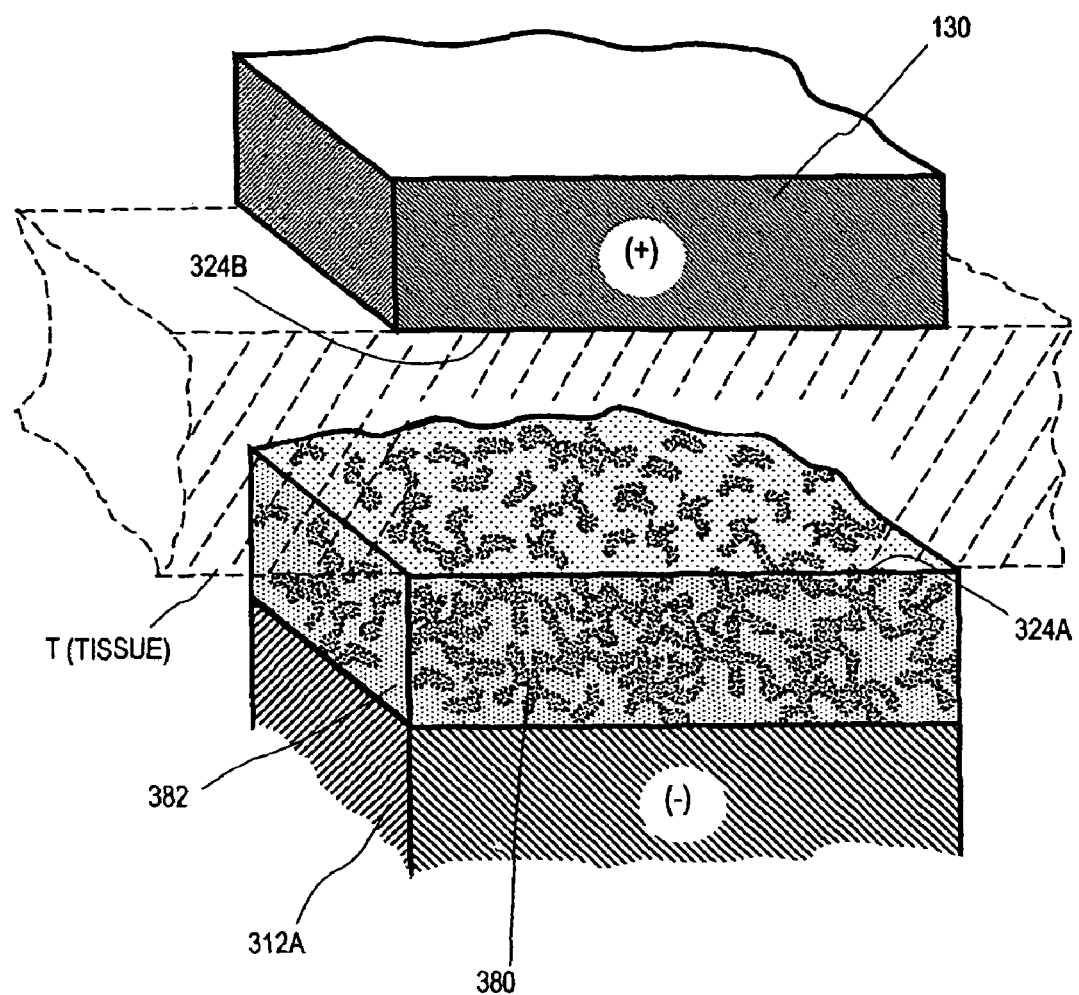
FIG. 24 is a view of an alternative matrix wherein the first and second PTCR compositions have a random distribution.

It should be further appreciated that the matrix in one or both engagement surfaces 324A and 324B (see FIG. 15) can be a more random distribution of first and second PTCR compositions 380 and 382 as depicted in FIG. 24. These first and second PTCR compositions 380 and 382 can respective first switching range between 80°-120° C., and a second switching range between 120°-300° C. as described above. In the engagement surface 324A, the random spatial locations of the first and second PTCR compositions 380 and 382 can provide modulated energy application similar to that of the pixelated embodiments described above. Further, the elastic moduli of the respective first and second PTCR compositions 380 and 382 can vary exactly as described above in the dimensionally ordered matrices.

Figure 25:
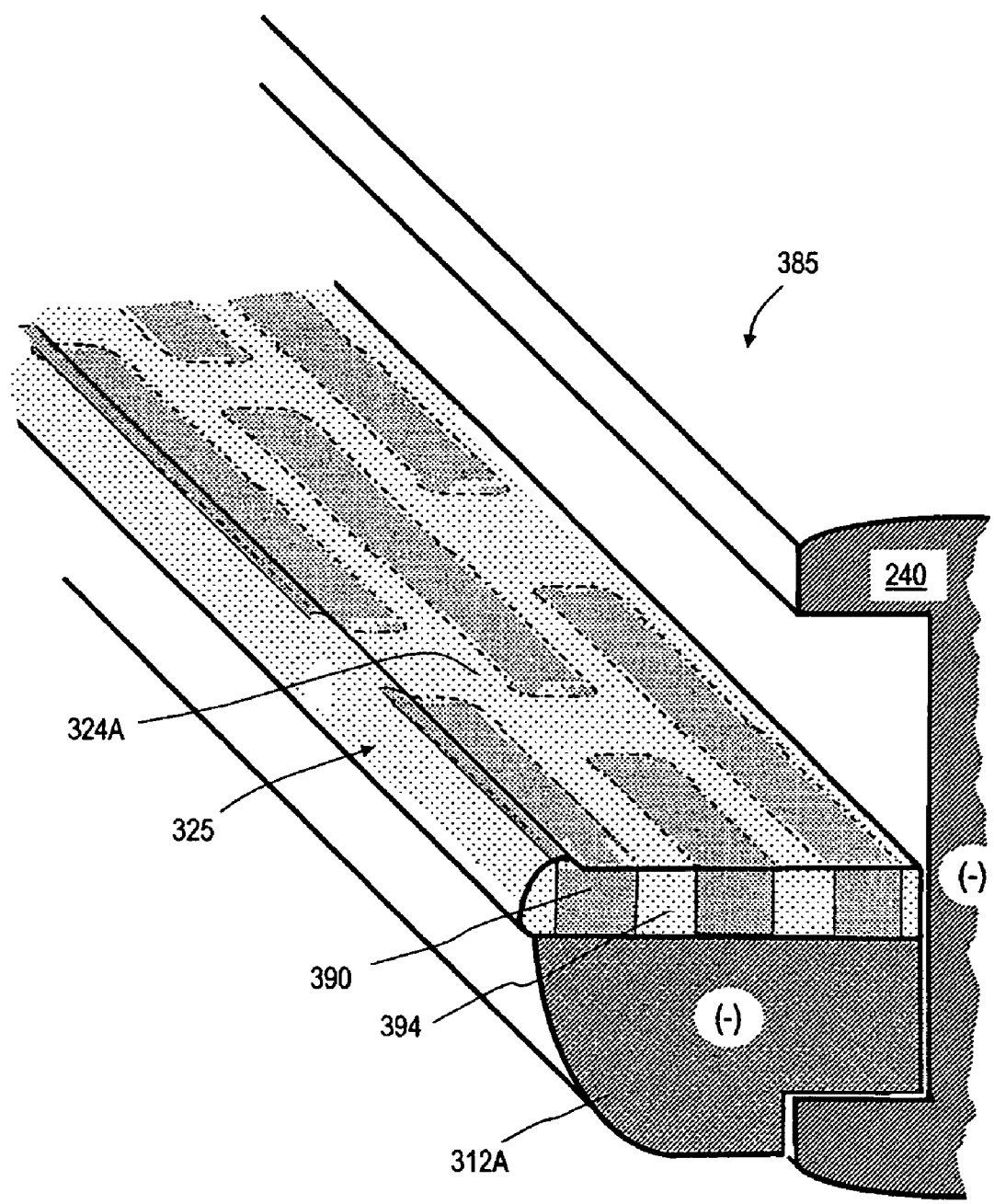
FIG. 25 is a perspective view of an alternative jaw engagement surface with a plurality of spaced apart PTCR regions for creating thermal "staple-like" weld features in a tissue margin.
Figure 26:
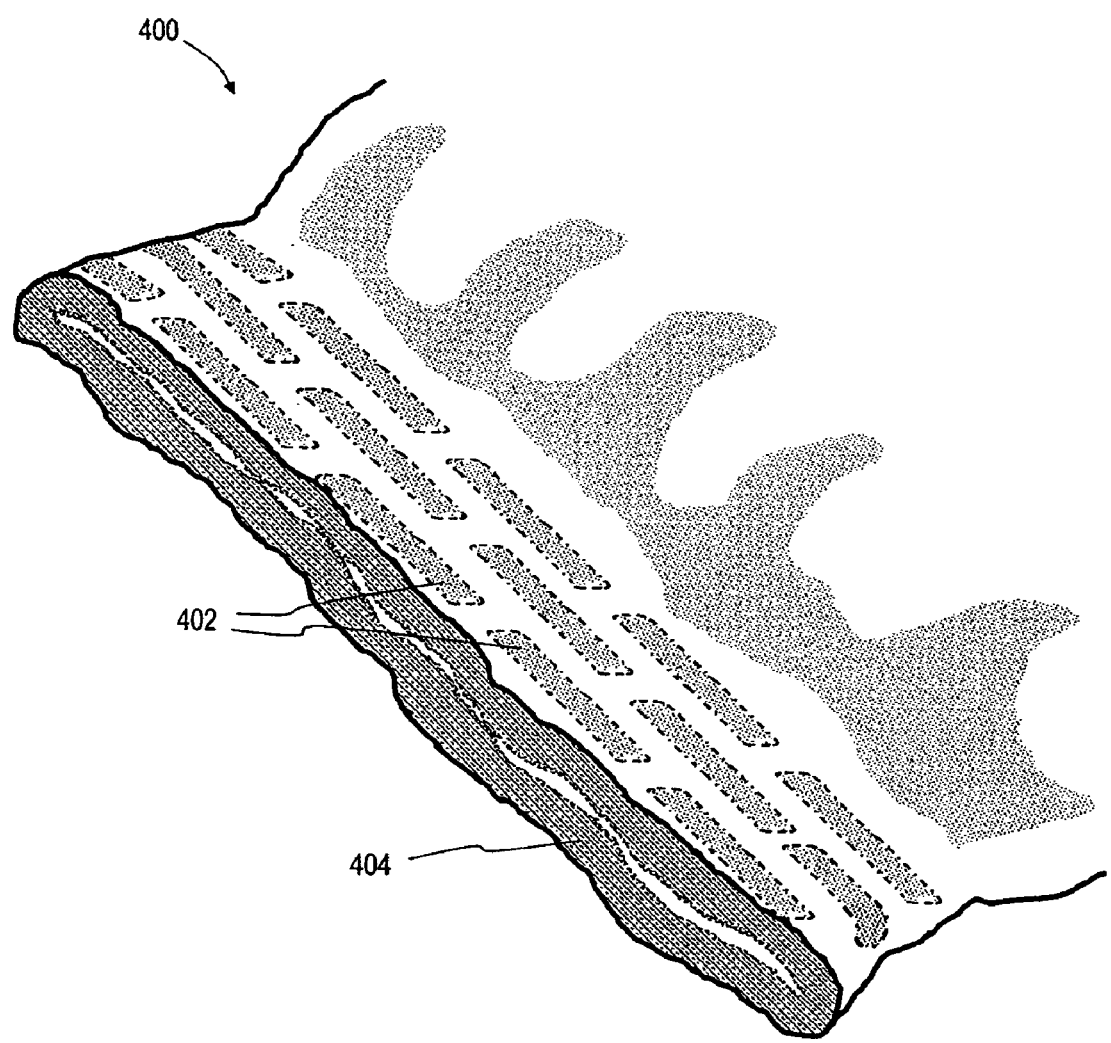
FIG. 26 is a schematic view of an organ margin with a plurality of thermal "staple-like" welds that is enabled by the working end of FIG. 25.

FIG. 25 illustrates another alternative jaw structure 385 with an engagement surface 324A that includes a plurality of spaced apart PTCR regions 390 for creating thermal "staple-like" welds in a tissue margin. The polymeric composition 394 of the field is preferably an insulative polymer but can also be a second PTCR material as described above. The spaced apart PTCR regions 390 typically can have a higher modulus as described above. FIG. 26 is a schematic illustration of an organ 400 treated with the jaw structure 385 of FIG. 25. It can be understood that the jaw structure would create a pattern of controllably shaped, controllably dimensioned and controllably spaced apart welds 402 in tissue, or along a transected tissue margin 404, to provide a seal. This manner of treating tissue has the advantage of providing an intermittent weld or seal which will allow the tissue to retain more elasticity and flexibility after being sealed. Such an intermittent weld or seal also may be advantageous in thin or fragile tissues. The use of such an intermittent weld or seal can be used treating various body organs, such as lung resections, thin-walled veins, bowels and other hollow or tubular organs.

The foregoing description of various embodiments of the invention has been presented for purposes of illustration and description. It is not intended to limit the invention to the precise forms disclosed. Many modifications, variations and refinements will be apparent to practitioners skilled in the art. Further, the teachings of the invention have broad application in the electrosurgical and laparoscopic device fields as well as other fields which will be recognized by practitioners skilled in the art.

Elements, characteristics, or acts from one embodiment can be readily recombined or substituted with one or more elements, characteristics or acts from other embodiments to form numerous additional embodiments within the scope of the invention Hence, the scope of the present invention is not limited to the specifics of the exemplary embodiment, but is instead limited solely by the appended claims.

What is claimed is:

1. An electrosurgical working end jaw structure for performing high strength welding of tissue, the working end comprising:

a body having a tissue contacting surface, the body including pixel portions and non-pixel portions distributed within the tissue contacting surface, the pixel portions comprising a first positive temperature coefficient of resistance (PTCR) material and the non-pixel portions comprise a second material having a second positive temperature coefficient of resistance and at least one pixel portion configured to switch Rf current on and off through the at least one pixel portion in response to tissue temperature adjacent the at least one pixel portion, the pixel portions configured to be coupled to an Rf current source and being adapted to deform a different amount in response to tissue applied force than the non-pixel portions.

2. The electrosurgical working end of claim 1, wherein the pixel portions are spaced apart by the non-pixel portions.

3. The electrosurgical working end of claim 1, wherein the pixel portions are each independently switchable.

4. The electrosurgical working end of claim 1, wherein the pixel portions comprises an array of pixel portions, the array configured to produce a substantially uniform thermal effect in tissue including at least one of tissue welding, tissue weld strength, ohmic heating or protein denaturation.

5. The electrosurgical working end of claim 1, wherein the pixel portions have a size or shape configured to control at least one of an electrical conductivity, a thermal conductivity, or a thermal response time of at least a portion of the body.

6. The electrosurgical working end of claim 1, wherein the first PTCR material has a switching range between about 70° C. and 90° C.

7. The electrosurgical working end of claim 1, wherein the pixel portions have a substantially rectangular, polygonal, circular or oval surface exposed shape.

8. The electrosurgical working end of claim 1, wherein the pixel portions and the non-pixel portions have a differing material property value.

9. The electrosurgical working end of claim 8, wherein the material property includes at least one of durometer or elastic modulus.

10. The electrosurgical working end of claim 9, wherein the non-pixel portions have a lower durometer or elastic modulus value than the pixel portions.

11. The electrosurgical working end of claim 8, wherein the differing material property value is configured to provide the tissue contacting surface with a mechanically dynamic tissue gripping capability.

12. The electrosurgical working end of claim 8, wherein the differing material property value is configured to produce recesses in the non-pixel portions when tissue contacting surface is engaged against tissue.

13. A working end of a surgical instrument for performing high strength welding of tissue, the working end comprising:
paired first and second jaw members moveable between an open position and a closed position; and
at least one jaw member including a tissue-contacting body having spaced apart regions of a first polymeric material exhibiting a positive temperature coefficient of resistance (PTCR) for responding to adjacent tissue temperature to thereby switch Rf current on and off at each region; and
wherein the spaced apart regions of the first polymeric material are distributed within a second polymeric material, and wherein the spaced apart region of the first polymeric material are adapted to deform a different amount in response to tissue applied force than the second polymeric material to produce recesses in the second polymeric material.

14. The working end of claim 13, wherein the spaced apart regions of the first polymeric material have an ordered arrangement within the second polymeric material.

15. The working end of claim 13, wherein the second polymeric material exhibits a positive temperature coefficient of resistance, a negative temperature coefficient of resistance or a fixed resistance.

16. The working end of claim 13, wherein the first and second polymeric material have a different durometer.

17. A method for welding tissue using Rf energy the method comprising:
engaging tissue with an energy delivery surface having current switchable regions dispersed within non-switchable regions, the switchable regions comprising a positive temperature coefficient of resistance material;
delivering Rf energy to the tissue so as to ohmically heat tissue,
switching RF current flow to tissue through at least one switchable region responsive to the temperature of ohmically heated tissue adjacent the at least one switchable region; and
producing a substantially uniform thermal effect in tissue, wherein the non-switching regions deform a different amount in response to tissue applied force than the switching regions; and
creating recesses in at least a portion of the non-switching regions by engaging the energy delivery surface with tissue;
capturing migrated tissue fluid in at least a portion of the recesses; and
hydrating engaged tissue during the delivery of Rf energy, utilizing the captured fluid.

18. The method of claim 17, wherein the switching occurs on a micron scale.

19. The method of claim 17, wherein the switching occurs responsive to at least one of an impedance or hydration level of tissue adjacent the at least one switchable region.

20. The method of claim 17, wherein the substantially uniform thermal effect is at least one of tissue welding, tissue weld strength, ohmic heating or protein denaturation.

21. The method of claim 17, further comprising:
creating regionalized current densities in the engaged tissue which correlate to the switchable regions.

22. The method of claim 17, wherein the non-switching regions deform a different amount in response to tissue applied force than the switching regions to facilitate engagement of tissue during the application of force and Rf energy.

* * * * *